US006737057B1

(12) United States Patent
Zaghouani

(10) Patent No.: US 6,737,057 B1
(45) Date of Patent: May 18, 2004

(54) COMPOUNDS, COMPOSITIONS AND METHODS FOR THE ENDOCYTIC PRESENTATION OF IMMUNOSUPPRESSIVE FACTORS

(75) Inventor: Habib Zaghouani, Knoxville, TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 08/779,767

(22) Filed: Jan. 7, 1997

(51) Int. Cl.[7] .......... A61K 39/395

(52) U.S. Cl. .......... 424/134.1; 424/133.1; 424/178.1; 424/180.1; 530/387.3

(58) Field of Search .......... 424/178.1, 180.1

(56) References Cited

U.S. PATENT DOCUMENTS

| | | | | |
|---|---|---|---|---|
| 5,474,771 A | | 12/1995 | Lederman et al. | 424/133.1 |
| 5,508,386 A | * | 4/1996 | Zanetti et al. | 530/387.3 |
| 5,612,035 A | | 3/1997 | Howell et al. | 424/185.1 |

FOREIGN PATENT DOCUMENTS

| | | | |
|---|---|---|---|
| EP | 0 629 703 | | 12/1994 |
| GB | 90/02017 | * | 7/1991 |
| WO | WO 92/05793 | | 4/1992 |
| WO | WO 93/06135 | | 4/1993 |
| WO | WO 93/10220 | | 5/1993 |
| WO | WO 94/10332 | | 5/1994 |
| WO | 9414847 | | 7/1994 |
| WO | WO 94/28027 | | 12/1994 |
| WO | WO 95/23814 | | 9/1995 |
| WO | 9616086 | | 5/1996 |
| WO | WO 96/19584 | | 6/1996 |
| WO | WO 96/34622 | | 11/1996 |
| WO | WO 99/09064 | | 2/1999 |

OTHER PUBLICATIONS

Rudikoff et al Proc Natl Acad Sci USA vol. 179 1979, 1982.*

Panak et al Proc Natl Acad Sci USA vol. 85 3080–3084, May 1988.*

Livingstone et al Ann Rev Immuno vol. 5 477–501, 1987.*

Hurtenbach et al. J Exp Medicine vol. 177 1499–1504, 1993.*

Bona et al Cellular and Molecular Biology vol. 40 Suppl I 21–30, 1994.*

Legge et al J Exp Medi vol. 185 No 6 1043–1053, Mar. 1997.*

Kuchroo et al. J. of Immunology, vol. 153:3326–3336, 1994.*

Arnold et al., Multiple levels of peripheral tolerance, *Immunol. Today,* 14:12–14 (1993).

Fowlkes et al., T–cell tolerance, *Curr. Opin. Immunol.,* 5:873–879 (1993).

Jenkins et al., Molecules Involved in T–cell costimulation, *Curr. Opin. Immunol.,* 5:361–367 (1993).

Kosaka et al., Tolerance of CD8+ T Cells Developing in Parent F1 Chimerae Prepared with Supralethal Irradiation: Step–Wise Induction of Tolerance in the Intrathymic and Extrathymic Environments, *J. Exp. Med.,* 177:367–378 (1993).

McCormack et al., Profound Deletion of Mature T Cells in Vivo by Chronic Exposure to Exogenous Superantigen, *J. Immunol.,* 150:3785–3792 (1993).

Rocha et al., Peripheral Selection of the T Cell Repertoire, *Science* (Washington, D.C.), 251:1225–1228 (1991).

Webb et al., Extrathymic Tolerance of Mature T Cells: Clonal Elimination as a Consequence of Immunity, *Cell.,* 83:1249–1256 (1990).

Zaghoueni et al., Cells expressing an H Chein Ig Gene Carrying a Viral T Cell Epitope are Lysed by Specific cytolytic T Cells, *J. Immunol.,* 148:3604–3609 (1992).

Zaghouani et al., Presentation of a Viral T Cell Epitope Expressed in the CDR3 Region of a Self Immunoglobulin Molecule, *Science,* 259:224–227 (1993).

Zaghouani et al., Induction of antibodies to the envelope protein of the human immunodeficiency virus by immuniation with monoclonal anti–idotypes, *Proc. Natl. Acad. Sci USA.* 88:5845–5849 (1991).

Adorini, et al., New Perspectives on Immunointervention in Autoimmune Diseases, Immunol. Today, 11(11):383–386 (1990).

Endoh, et al., Studies of Experimental Allergic Encephalomyelitis in Old Mice, J. of Neuroimmunol., 29:21–31 (1990).

Gosselin, et al., Enhanced Antigen Presentation Using Human Fogamma Receptor (Monocyte/Macrophage)–Specific Immunogens. J. Immunol., 149(11):3477–3481 (1992).

Muller, et al., Selective in vivo Inhibition of T Cell Activation by Class II MHC–Binding Peptides Administered in Soluble Form, J. Immunol., 145(12):4006–4011 (1990).

Riechmann, et al., Reshaping human Antibodies for therapy, Nature, vol. 332, Mar. 24: 323–327 (1988).

Sollazzo, et al., Expression of an exogenous peptide epitope genetically engineered in the variable domain of an immunoglobulin: implications for antibody and peptide folding, Protein Engineering, vol. 4, No. 2: 215–220 (1990).

(List continued on next page.)

*Primary Examiner*—Patrick J. Nolan

(57) ABSTRACT

Immunomodulating agents comprising at least one Fc receptor ligand and at least one immunosuppressive factor are provided as are methods for their manufacture and use. The immunomodulating agents may be in the form of polypeptides or chimeric antibodies and preferably incorporate an immunosuppressive factor comprising a T cell receptor antagonist. The compounds and compositions of the invention may be used to selectively suppress the immune system to treat symptoms associated with immune disorders such as allergies, transplanted tissue rejection and autoimmune disorders including lupus, rheumatoid arthritis and multiple sclerosis.

16 Claims, 9 Drawing Sheets

OTHER PUBLICATIONS

Takemori, et al., Mechanism of Neonatally Induced Idiotype Suppression and its Relevance for the Acquistion of Self–tolerance, Immunological Reviews, 79:103–117.

Zaghouani, et al., Engineered Immunoglobulin Molecules as Vehicles for T Cell Epitopes, Intern. Rev. Immunol., 10:265–278 (1993).

Zaghouani, Habib, U.S. App. No. 10/000,868, filed Nov. 30, 2001, entitled "Compounds, Compositions and Methods for the Endocytic Presentation of Immunosuppressive Factors," Docket No. ALLIA, 143DV1.

International Search Report for co–pending Application No PCT/US01/40834.

Min, et al. "Modulation in Vivo of Autoreactive T Cells by a TCR Antagonist Ig Chimera" J. of Allergy & Clinical Immunology 99(1):738 (Jan. 1997).

Ashton–Richards, et al. "Evidence for a Differential Avidity Model of T Cell Selection in the Thymus" Cell 76:651–663 (1994).

Brocke, et al. "Treatment of Experimental Encephalomyelitis with a Peptide Analogue of Myelin Basic Protein" Nature 379: 343–346 (Jan. 25, 1996).

Chou, et al. "Frequency of T Cells Specific for Myelin Basic Protein and Myelin Proteolipid Protein in Blood and Cerebrospinal Fluid in Multiple Sclerosis" J. of Neuroimmunology 38: 105–114 (1992).

Cibotti, et al. "Tolerance to a Self–Protein Involves Its Immunodominant But Does Not Involve Its Subdominant Determinants" Proc. Natl. Acad. Sci. USA 89:416–420 (1992).

De Magistris, et al., "Antigen Analog–Major Histocompatibility Complexes Act as Antagonists of the T Cell Receptor" Cell 68:625–634 (1992).

Evavold, et al. "Tickling the TCR: Selective T–Cell Functions Stimulated by Altered Peptide Ligands" Immunology Today 14(12): 602–609 (1993).

Evavold, et al. "Seperation of IL–4 Production From Th Cell Proliferation by an Altered T Cell Receptor Ligand" Science 252: 1308–1310 (1991).

Feldman, et al. "Rheumatoid Arthritis" Cell 85: 307–310 (May 3, 1996).

Hsu, et al. "Modulation of T Cell Development by an Endogenous Altered Peptide Ligand" J. Exp. Med. 181:805–810 (1995).

Jameson, et al. "Clone–Specific T Cell Receptor Anagonists of Major Histocompatibility Complex Class I–Restricted Cytotoxic T Cells" J. Exp. Med 177: 1541–1550 (1993).

Jameson, et al. "Positive Selection of Thymocytes" Annu. Rev. Immunol. 13:93–126 (1995).

Klassen, et al. "Blood Flow and Tissue Space of the Left Coronary Artery in Man" Circulation Res. 27: 185–195 (1970).

Kuchroo, et al. "Experimental Allergic Encephalomyelitis Mediated by Cloned T Cells Specific for a Synthetic Peptide of Myelin Proteolipid Protein" J. of Immunology 148(12):3776–3782 (1992).

Kuchroo, et al. "A Single TCR Anagonist Peptide Inhibits Experimental Allergic Encephalomyelitis Mediated by a Diverse T Cell Repertoire" J. of Immunology 153:3326–3336 (1994).

Liu, et al. "Low Avidity Recognition of Self–Antigen by T Cells Permits Escape from Central Tolerance" Immunity 3: 407–415 (1980).

Mamula, Mark J. "The Inability to Process a Self–Peptide Allows Autoreactive T Cells to Escape Tolerance" J. Exp. Med. 177:567–571 (1993).

Martin et al. "Immunological Aspects of Demyelinating Diseases" Annu. Rev. Immunol. 10: 153–187 (1992).

McRae, et al. "Functional Evidence for Epitope Spreading on the Relapsing Pathology of Experimental Autoimmune Encephalomyelitis" J. Exp. Med. 182: 75–85 (1995).

Sebzda, et al. "Positive and Negative Thymocyte Selection Induced by Different Concentration of a Single Peptide" Science 263: 1615–1618 (1994).

Sercarz, et al. "Dominance and Crypticity of T Cell Antigenic Derminants" Annu. Rev. Immunol. 11: 729–766 (1993).

Steinman, Lawrence "Multiple Sclerosis: A Coordinated Immunological Attack Against Myelin in the Central Nervous System" Cell 85: 299–302 (May 3, 1996).

Tisch, et al. "Insulin–Dependent Diabetes Mellitus" Cell 85: 291–297 (May 3, 1996).

Tuohy, et al. "Identification of an Encephalitogenic Determinant of Myelin Proteolipid Protein for SJL Mice" J. of Immunology 142(5): 1523–1527 (1989).

Windhagen, et al. "Modulation of Cytokine Patterns of Human Autoreactive T Cell Clones by a Single Amino Acid Substitution of Their Peptide Ligand" Immunity 2: 373–380 (1995).

Wucherpfenning, et al. "Molecular Mimicry in T Cell–Mediated Autoimmunity: Viral Peptides Activate Human T Cell Clones Specific for Myelia Basic Protein" Cell 80: 695–705 (1995).

Zhang, et al. "Increased Frequency of Interleukin 2–Responsive T Cells Specific for Myelin Basic Protein and Proteolipid Protein in Peripheral Blood and Cerebrospinal Fluid of Patients with Multiple Sclerosis" J. Exp. Med. 179: 973–984 (1994).

Liu, C. et al. (1996) FcγRI–targeted fusion proteins result in efficient presentation by human monocytes of antigenic and antagonist T cell epitopes J. Clin. Invest. 98(9):2001–2007.

Min, B. et al., (1998) Neonatal exposure to a self–peptide–immunoglobulin chimera circumvents the use of adjuvant and confers resistance to autoimmune disease by a novel mechanism involving interleukin 4 lymph node deviation and interferon γ–mediated splenic anergy. J. Exp. Med. 188(11):2007–2017.

Legge, et al (1997) Presentation of a T–cell receptor antagonist peptide by immunoglobulins ablates activation of T cells by a synthetic peptide or protein requiring endoycytic processing J Exp Med 185(6) 1043–1053.

(May 8, 2000) PCT International Search Report in 6 pages Courtesy Copy.

Liu et al. "Affinity for class II MCH determines the extent to which soluble peptides tolerize autoreactive T cells in naive and primed adult mice—implications for autoimmunity" Int. Imm. 7(8) 1255–1263 (1995).

Karpus et al. "Inhibition of Relapsing Experimental Autoimmune Encephalomyelitis in SJL Mice by Feeding the Immunodominant PLP 139–151 Peptide" J. Neurosci. Res. 45: 410–423 (1996).

Karin et al. "Reversal of Experimental Autoimmune Encephalomyelitis by a Soluble Peptide Variant of a Myeline Basic Protine Epitope. T Cell Receptor Antagonism and Reduction of Interferon γ and Tumor Necrosis Factor α Production" J. Exp. Med. 180 2227–2237 (1994).

* cited by examiner

Figs. 7a-7b
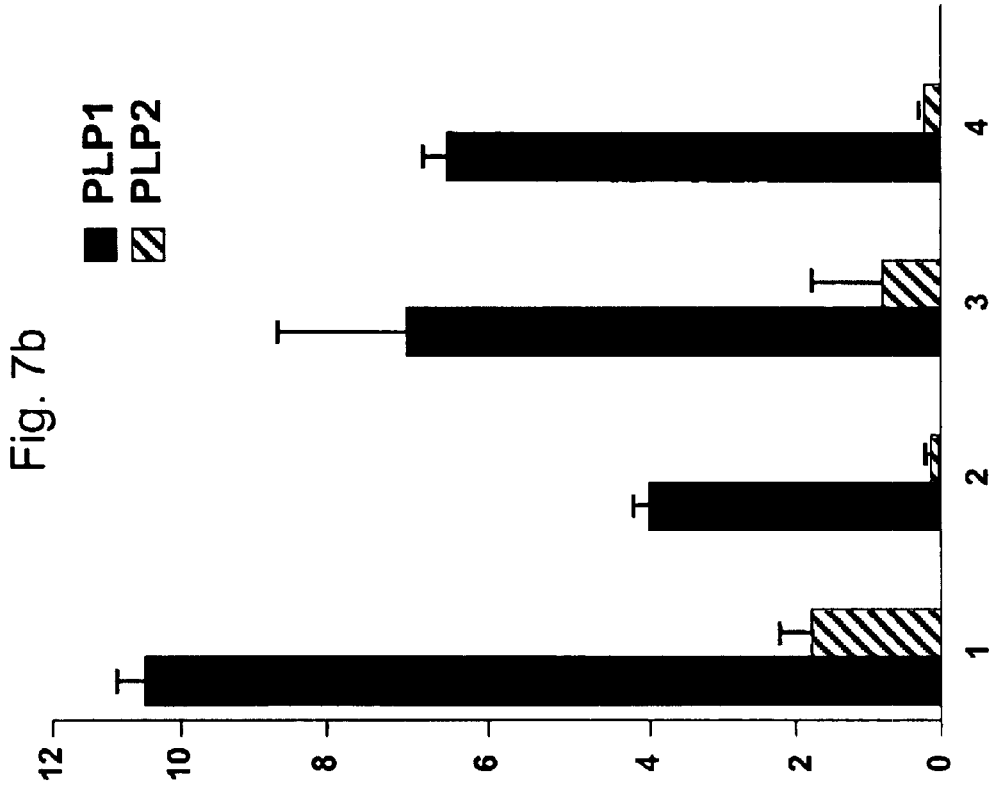
Fig. 7a
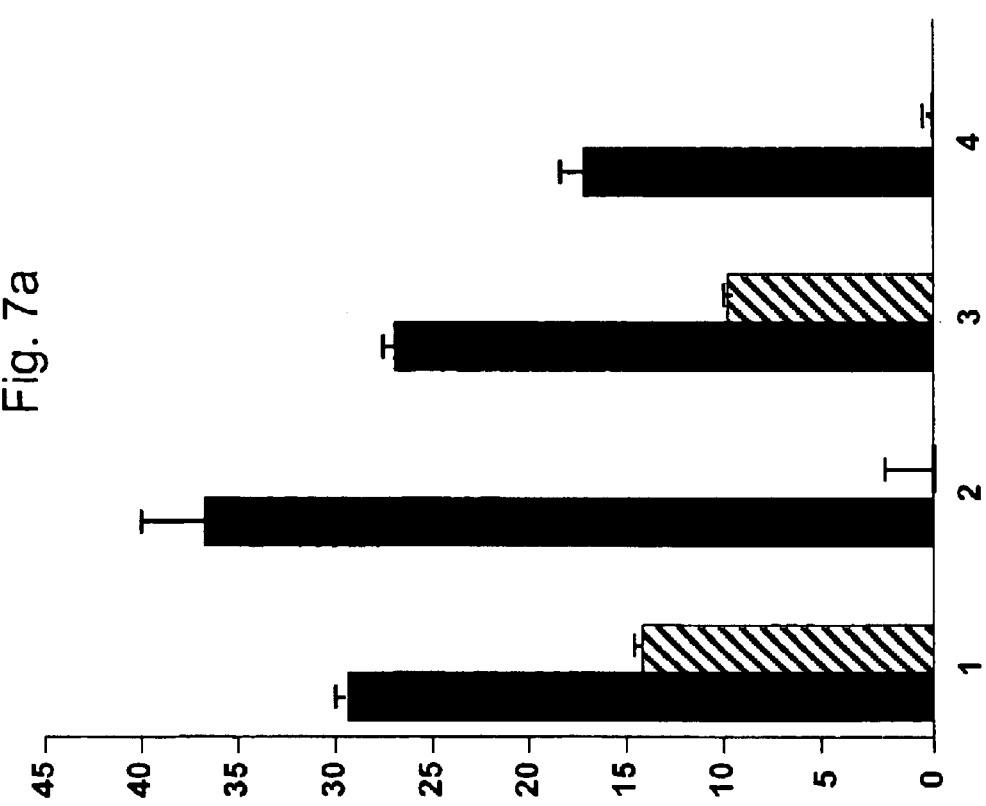
Fig. 7b

Figs. 9a-9b
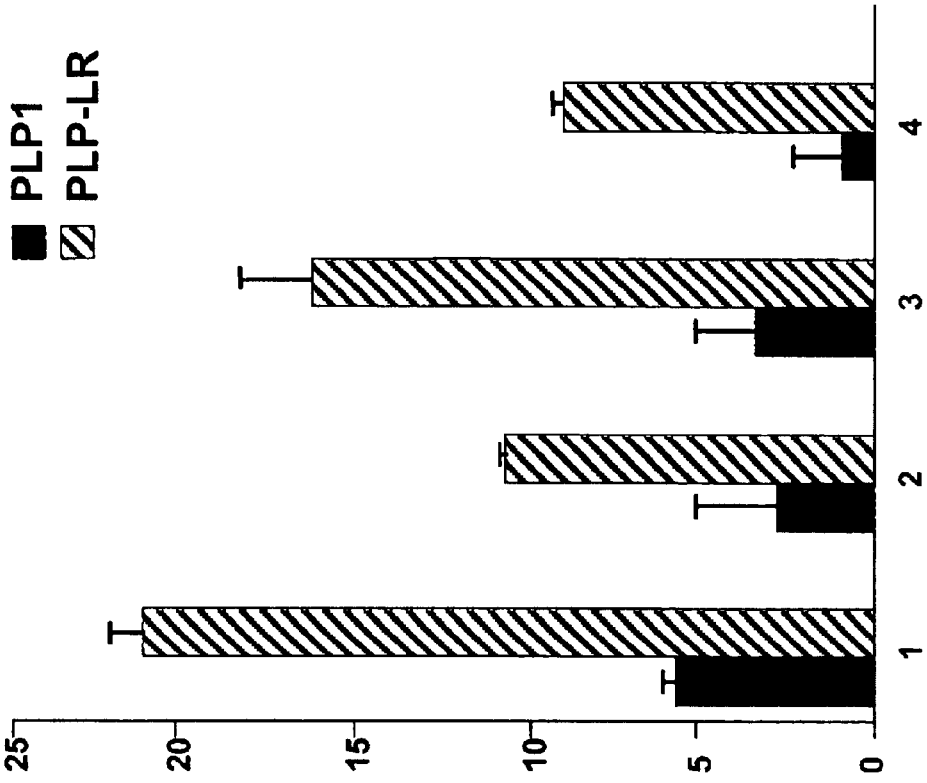
Fig. 9a
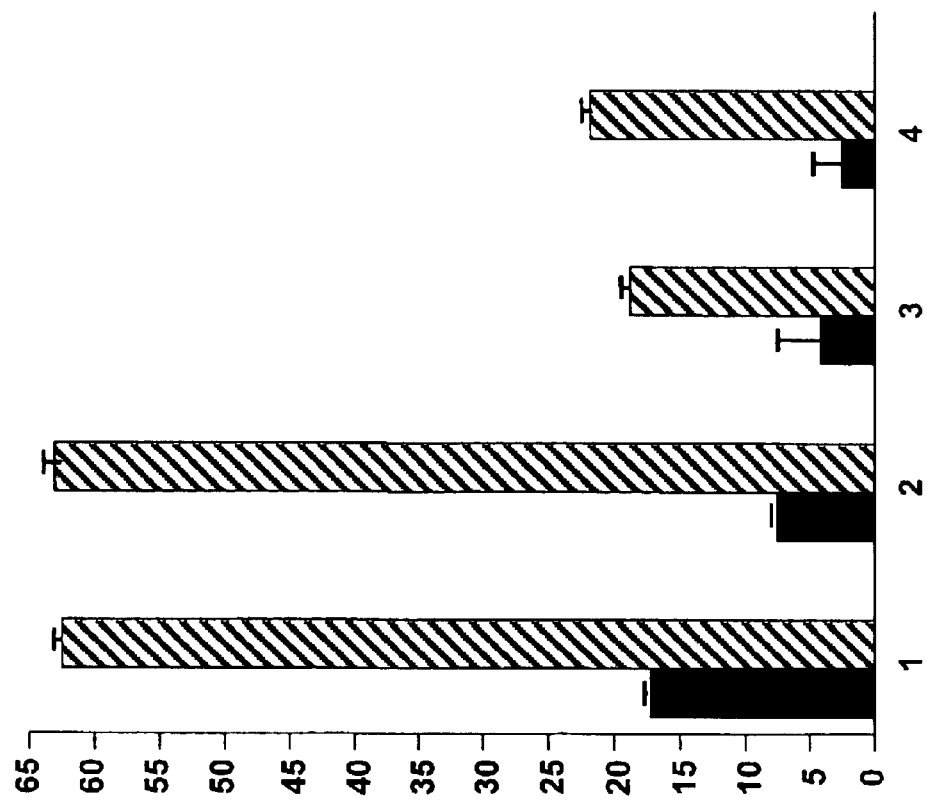
Fig. 9b

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Synthetic

<400> SEQUENCE: 1

His Ser Leu Gly Lys Trp Leu Gly His Pro Asn Lys Phe
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Synthetic

<400> SEQUENCE: 2

His Ser Leu Gly Lys Leu Leu Gly Arg Pro Asn Lys Phe
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Asn Thr Trp Thr Thr Cys Gln Ser Ile Ala Phe Pro Ser Lys
 1               5                  10
```

COMPOUNDS, COMPOSITIONS AND METHODS FOR THE ENDOCYTIC PRESENTATION OF IMMUNOSUPPRESSIVE FACTORS

FIELD OF THE INVENTION

The present invention generally relates to compounds, compositions and methods for the effective endocytic presentation of immunosuppressive factors. More particularly, the present invention is directed to compounds, methods and compositions comprising immunosuppressive factors that are useful for the treatment of various disorders including, but not limited to, autoimmune disorders. In preferred embodiments the immunosuppressive factors are T cell receptor antagonists.

BACKGROUND OF THE INVENTION

Vertebrates possess the ability to mount an immune response as a defense against pathogens from the environment as well as against aberrant cells, such as tumor cells, which develop internally. The immune response is the result of complex interactions between a variety of cells and factors, but generally comprises two main facets. One is a cellular component, in which specialized cells directly attack an offending agent (bearing an antigen) while the other is a humoral component, in which antibody molecules bind specifically to the antigen and aid in its elimination. Acting in concert, the individual elements are quite effective in limiting the initial onslaught of invading pathogens and eliminating them from the host.

The primary cells involved in providing an immune response are lymphocytes which generally comprise two principal classes. The first of these, designated B cells or B lymphocytes, are typically generated in bone marrow and are, among other duties, responsible for producing and secreting antibodies. B cell antibody products tend to react directly with foreign antigens and neutralize them or activate other components of the immune systems which then eliminate them. In particular, opsonizing antibodies bind to extracellular foreign agents thereby rendering them susceptible to phagocytosis and subsequent intracellular killing. On the other hand T cells or T lymphocytes, which generally develop or mature in the thymus, are responsible for mediating the cellular immune response. These cells do not recognize whole antigens but, instead, respond to short peptide fragments thereof bound to specialized proteins which appear on the surface of the surface of a target cell. More particularly, it appears that proteins produced within the cell, or taken up by the cell from extracellular milieu, are continually degraded to peptides by normal metabolic pathways. The resulting short fragments associate with intracellular major histocompatibility complex (MHC) molecules and the MHC-peptide complexes are transported to the surface of the cell for recognition by T cells. Thus, the cellular immune system is constantly monitoring a full spectrum of proteins produced or ingested by the cells and is posed to eliminate any cells presenting foreign antigens or tumor antigens; i.e. virus infected cells or cancer cells.

The general structure of immunoglobulin G (IgG), the most common of mammalian antibodies, is shown schematically in FIG. 1. As illustrated, IgG is a tetrameric protein complex comprising two identical heavy (H) chains and two identical immunoglobulin light (L) chains. These chains are joined together by disulfide bonds to form the Y-shaped antibody complex. In solution however, the molecule takes on a more globular shape and readily bind to foreign antigens present in biological fluids. Amino acid sequence analysis of immunoglobulins has led to the definition of specific regions with various functional activities within the chains. Each light chain and each heavy chain has a variable region ($V_L$ and $V_H$ respectively) defined within the first 110 amino terminal residues. Three dimensional pairing of the $V_L$ and $V_H$ regions constitute the antigen-recognition portion or "antigen combining site" ("ACS") of immunoglobulin molecule. Because of the tetrameric nature of immunoglobulins, there are two identical antigen combining sites per molecule. The variable domains of these chains are highly heterogeneous in sequence and provide the diversity for antigen combining sites to be highly specific for a large variety of antigenic structures. The heterogeneity of the variable domains is not evenly distributed throughout the variable regions, but is located in three segments, called complementarity determining regions ("CDRs") designated CDR 1, CDR 2 and CDR 3. For further information regarding these structures see Watson et al., 1987, *Molecular Biology of the Gene,* Fourth Edition, Benjamin/Cummings Publishing Co., Inc. Menlo Park, Calif. incorporated herein by reference.

Each of the heavy chains also includes a constant region defining a particular isotype and assigns the immunoglobulin to one of the immunoglobulin classes and subclasses. The constant region contains units called domains (i.e. $C_{H1}$, $C_{H2}$, etc.) which do not vary significantly among antibodies of a single class. The constant region does not participate in antigen binding, but can be associated with a number of biological activities known as "effector functions", such as binding to Fc receptors on cell surfaces of antigen presenting cells (APC's) as well as binding to complement proteins. Antigen presenting cells such as dendritic cells and macrophages are, among other features, generally distinguished by the presence of an Fc receptor. Consequently, if an antibody is bound to a pathogen, it can then link to a phagocyte via the Fc portion. This allows the pathogen to be ingested and destroyed by the phagocyte, a process known as opsonization. Moreover, as will be discussed in more detail below, various pathogenic antigens may be processed and displayed by the APC to further stimulate an immune response.

Unlike the heavy chains, the light chains have a single constant domain ($C_L$). A light chain pairs with a heavy chain through a disulfide bond which attaches heavy constant region $C_{H1}$ to $C_L$. In addition, the heavy chains have a hinge region separating constant regions $C_{H1}$ and $C_{H2}$ from the remainder of the molecule. It is this hinge region that is largely responsible for the flexibility of the tetramer. The two heavy chains of the molecule pair together through disulfide bonds at the junction between the hinge region and $C_{H2}$.

In order to provide such an extensive repertoire, immunoglobulin genes have evolved so as permit the production of vast numbers of different immunoglobulin proteins from a finite number of genes i.e. inherent polymorphism. Due to inherent polymorphism, mammals are able to produce antibodies to a seemingly infinite variety of antigens. For a review of immunoglobulin genetics and protein structure see Lewin, "Genes III", John Wiley and Sons, N.Y. (1987) and Benjamini and Leskowitz, 1988, Immunology, Alan R. Liss, Inc., New York which is incorporated herein by reference.

In the past few years antibodies have become extremely important in diagnostic and therapeutic applications due to their diversity and specificity. Increasingly, molecular biology techniques have been used to expand the variety and availability of antibodies for scientific applications. For instance, a single antibody producing B cell can be immortalized by fusion with a tumor cell and expanded to provide an in vitro source of antibodies of a single specificity known as a "monoclonal antibody" (mAb). Such an immortal B cell line is termed a "hybridoma."

Until recently, the source of most mAb has been murine (mouse) hybridomas cultured in vitro. That is, a mouse was typically injected with a selected antigen or immunogen. Subsequently, the animal was sacrificed and cells removed from its spleen were fused with immortal myeloma cells. Although they have been used extensively in diagnostic procedures, murine mAb are not well suited for therapeutic applications in most mammals including humans. In part, this is due to the fact that murine antibodies are recognized as foreign by other mammalian species and elicit an immune response which may itself cause illness.

To overcome at least some of the problems of immune responses generated by foreign mAb and the lack of suitable human mAb, genetic engineering has been used to construct humanized chimeric immunoglobulin molecules which contain the antigen binding complementarity determining regions of the murine antibodies but in which the remainder of the molecule is composed of human antibody sequences which are not recognized as foreign. Such antibodies have been used to treat tumors as the mouse variable region recognizes the tumor antigen and the humanized portion of the molecule is able to mediate an immune response without being rapidly eliminated by the body. See, for example, Jones et al., Nature, 321:522–525 (1986) which is incorporated herein by reference.

Other uses of such antibodies are detailed in co-pending U.S. Ser. No. 08/363,276 and PCT Publication No. WO 94/14847 which are also incorporated herein by reference. In these cases epitopes of foreign antigens such as viral or bacterial epitopes are grafted onto the hypervariable region of an immunoglobulin to induce a response. That is, the engineered antibodies are used as a vaccine to provoke an immune response and confer long term immunogenic memory thereby allowing the subject to fight off subsequent infections.

These and more traditional vaccines are effective in that they stimulate both prongs of the immune system. Despite the intricacies associated with the humoral component of the immune response, it would not, in and of itself, be capable of effectively protecting an animal from the myriad pathogenic assaults to which it is subject each day. Rather, it is only the presence of a highly evolved cellular response that allows higher organisms to survive and proliferate.

As indicated above, T lymphocytes or T cells, which arise from precursors in the bone marrow, are central players in the immune response against invading viruses and other microbes. The progenitor stem cells migrate to the thymus where, as so-called thymocytes, they become specialized. In particular, they begin to display the receptor molecules that later enable mature T cells to detect infection. To be beneficial, T cells must be able to attach through their receptors to microbial antigens (protein markers signaling an invader's presence). At the same time, they should be blind to substances made by the body as self-reactive T cells can destroy normal tissues. Typically, only those thymocytes that make useful receptors will mature fully and enter the bloodstream to patrol the body. Others that would be ineffectual or would attack the body's own tissue are, in healthy individuals, eliminated through apoptosis prior to leaving the thymus.

Mature T cells that finally enter the circulation, either as cytolytic T lymphocytes or T helper cells, remain at rest unless they encounter antigens that their receptors can recognize. Upon encountering the specific antigens for which the lymphocytes have affinity, they proliferate and perform effector functions, the result of which is elimination of the foreign antigens.

T cells have been classified into several subpopulations based on the different tasks they perform. These subpopulations include helper T cells ($T_h$), which are required for promoting or enhancing T and B cell responses; cytotoxic (or cytolytic) T lymphocytes (CTL), which directly kill their target cells by cell lysis; and suppressor T cells ($T_s$) which down-regulate the immune response. In every case T cells recognize antigens, but only when presented on the surface of a cell by a specialized protein complex attached to the surface of antigen presenting cells. More particularly, T cells use a specific receptor, termed the T cell antigen receptor (TCR), which is a transmembrane protein complex capable of recognizing an antigen in association with the group of proteins collectively termed the major histocompatibility complex (MHC). Thousands of identical TCR's are expressed on each cell. The TCR is related, both in function and structure, to the surface antibody (non-secreted) which B cells use as their antigen receptors. Further, different subpopulations of T cells also express a variety of cell surface proteins, some of which are termed "marker proteins" because they are characteristic of particular subpopulations. For example, most $T_h$ cells express the cell surface CD4 protein, whereas most CTL and $T_s$ cells express the cell surface CD8 protein. These surface proteins are important in the initiation and maintenance of immune responses which depend on the recognition of, and interactions between, particular proteins or protein complexes on the surface of APCs.

For some time it has been known that the major histocompatibility complex or MHC actually comprises a series of glycosylated proteins comprising distinct quaternary structures. Generally, the structures are of two types: class I MHC which displays peptides from proteins made inside the cell (such as proteins produced subsequent to viral replication), and class II MHC, which generally displays peptides from proteins that have entered the cell from the outside (soluble antigens such as bacterial toxins). Recognition of various antigens is assured by inherited polymorphism which continuously provides a diverse pool of MHC molecules capable of binding any microbial peptides that may arise. Essentially, all nucleated cells produce and express class I MHC which may exhibit naturally occurring peptides, tumor associated peptides or peptides produced by a viral invader. Conversely, only a few specialized lymphoid cells, those generally known as antigen presenting cells, produce and express class II MHC proteins. Regardless of the cell type, both classes of MHC carry peptides to the cell surface and present them to resting T lymphocytes. Ordinarily, $T_h$ cells recognize class II MHC-antigen complexes while CTL's tend to recognize class I MHC-antigen complexes.

When a resting T cell bearing the appropriate TCR encounters the APC displaying the peptide on its surface, the TCR binds to the peptide-MHC complex. More particularly, hundreds of TCR's bind to numerous peptide-MHC complexes. When enough TCRs are contacted the cumulative effect activates the T cell. Receptors on T cells that are responsible for the specific recognition of, and response to, the MHC-antigen complex are composed of a complex of several integral plasma membrane proteins. As with the MHC complex previously discussed, a diverse pool of TCR's is assured by inherent polymorphism leading to somatic rearrangement. It should be emphasized that, while the pool of TCR's may be diverse, each individual T cell only expresses a single specific TCR. However, each T cell typically exhibits thousands of copies of this receptor, specific for only one peptide, on the surface of each cell. In addition, several other types of membrane associated proteins are involved with T cell binding and activation.

Activation of the T cell entails the generation of a series of chemical signals (primarily cytokines) that result in the cell taking direct action or stimulating other cells of the immune system to act. In the case of class I MHC-antigen activation, CTL's proliferate and act to destroy infected cells presenting the same antigen. Killing an infected cell deprives a virus of life support and makes it accessible to antibodies, which finally eliminate it. In contrast, activation of $T_h$ cells by class II MHC-antigen complexes does not destroy the antigen presenting cell (which is part of the host's defense system) but rather stimulates the $T_h$ cell to proliferate and generate signals (again primarily cytokines) that affect various cells. Among other consequences, the signaling leads to B cell stimulation, macrophage activation, CTL differentiation and promotion of inflammation. This concerted response is relatively specific and is directed to foreign elements bearing the peptide presented by the class II MHC system.

When operating properly the immune response is surprisingly effective at eliminating microscopic pathogens and, to a lesser extent, neoplastic cells. In general, the complicated mechanisms for self-recognition are very efficient and allow a strong response to be directed exclusively at foreign antigens. Unfortunately, the immune system occasionally malfunctions and turns against the cells of the host provoking an autoimmune response. Typically, autoimmunity is held to occur when the antigen receptors on immune cells recognize specific antigens on healthy cells and cause the cells bearing those particular substances to die. In many cases, autoimmune reactions are self-limited in that they disappear when the antigens that set them off are cleared away. However, in some instances the autoreactive lymphocytes survive longer than they should and continue to induce apoptosis or otherwise eliminate normal cells. Some evidence in animals and humans indicates that extended survival of autoreactive cells is implicated in at least two chronic autoimmune disorders, systemic lupus erythematosus and rheumatoid arthritis.

Other mechanisms of action are also thought to contribute to the development of various autoimmune disorders. For example, over the last few years it has become clear that the avidity of T cell-APC interactions dictates thymic learning and tolerance to self antigens. Accordingly, high avidity interactions lead to elimination of the T cell whereas low avidity interactions allow for maturation and exit from the thymus. Although this mechanism is effective in purging the immune system of autoreactivity, T cell precursors endowed with self reactivity could still be generated and migrate to the periphery if the autoantigen is sequestered and does not achieve effective levels of thymic presentation, is subjected to thymic crypticity, or is poorly presented. Moreover, superantigens capable of reacting with particular T cell receptors and events that could stimulate antigen mimicry, epitope spreading or peripheral loosening in peptide crypticity may trigger activation of those self-reactive T cells and cause antigen exposure. In any case, continuous supply of autoantigen and abundant generation of T cell receptor ligands (peptide-MHC complexes) are a likely mechanism of T cell aggressivity. Examples of such a spontaneous break in self-tolerance include multiple sclerosis (MS), rheumatoid arthritis (possibly more than one mechanism) and type I diabetes all of which are thought to be T cell mediated autoimmune diseases.

Regardless of which mechanism is responsible for the corruption of the immune system, the results can be devastating to the individual. For example, multiple sclerosis is a chronic, inflammatory disorder that affects approximately 250,000 individuals in the United States. The inflammatory process occurs primarily within the white matter of the central nervous system and is mediated by T cells, B cells and macrophages which are responsible for the demyelination of the axons. Although the clinical course can be quite variable, the most common form is manifested by relapsing neurological deficits including paralysis, sensory deficits and visual problems.

Once immune cells have spread to the white matter of the central nervous system, the immune response is targeted to several different antigens on myelin. For example, there is a critical antibody response directed to myelin that activates the complement cascade with membrane attack complexes appearing in the spinal fluid. Further, T cells are targeted to certain key portions of various myelin antigens such as those presented on myelin basic protein (MBP) and proteolipid protein (PLP). The T cells in turn produce cytokines which then influence macrophages to attack the myelin and phagocytose large chunks of the myelin sheath. The concerted attack leads to areas of demyelination impairing salatory conduction along the axon and producing and the pathophysiologic defect. Multiple immune responses to several components of a supramolecular structure, like the myelin sheath in multiple sclerosis or the pyruvate dehydrogenase complex in primary biliary cirrhosis, are common in individuals with autoimmune diseases involving discrete organs.

Treatments for autoimmune diseases have met with varying levels of success. For example, it is often possible to correct organ-specific autoimmune disease through metabolic control. Where function is lost and cannot be restored, mechanical substitutes or tissue grafts may be appropriate. However, no effective treatments exist for several of the most disabling disorders including MS. While a number of compounds, including corticosterioids and modified beta interferon, can reduce some symptoms of MS, they have proven to have serious side effects or otherwise been shown to be less than desirable for long term use. Other avenues of treatment have shown promise but have yet to be shown effective.

In this respect, one promising treatment for MS is described in WO 96/16086, incorporated herein by reference, which discloses the use of peptide analogs of myelin basic protein (MBP). Compositions comprising these analogs are reportedly able to ameliorate symptoms of MS without excessive side effects. Moreover, use of peptide analogs to myelin constitutive proteins were also shown to be effective in treating the symptoms of experimental allergic encephalomyelitis (EAE), an organ specific immune disorder often used in mice as a model for MS. Specifically, reversal of EAE was achieved with a peptide analog derived from proteolipid (PLP) peptide (Kuchroo et al., *J. Immunol.* 153:3326–3336, 1994, incorporated herein by reference). It was shown that when the major TCR contacting residues within the naturally occurring PLP peptide were mutated, the resulting peptide analog bound MHC as well as the natural peptide yet does not activate PLP specific T cells. Instead the PLP analog inhibits in vitro activation of the T cells.

While peptide analogs represent an attractive approach to modulate the effector functions of aggressive T cells and ameliorate autoimmune diseases, several problems limit their effectiveness. For instance, only a few MHC-peptide complexes are available on the surface of a typical APC meaning a single complex may be required to serially trigger about 200 TCRs to activate the T cell. Where the autoantigen is continuously available for normal processing and presentation by the MHC system, it appears that very few surface MHC complexes would be available to bind the peptide analog. Further, as free peptides have very short half-lives, they are not readily incorporated and processed by the MHC-antigen presenting system, little will be naturally expressed on the APC. Due to the inefficient presentation, direct inhibition of the thousands of TCR's on each T cell likely require prohibitively high intracellular levels of free peptide. The turnover of cell surface MHC molecules also contributes to the short stay of complexes formed at the extracellular milieu (i.e. MHC class II molecules have been in the cell surface for some time before binding the extracellular peptide) while complexes formed in the endocytic compartment will reside for a normal period of time because they have just been translocated to the cell surface. Finally, administration of such synthetic epitopes or analogs is extremely problematic in view of the short half-life of peptides in the mammalian body. Between the short half-lives of the MHC complexes and the administered peptides, effective exposure is too brief to permit the induction of a satisfactory immune response further necessitating higher doses.

Accordingly, it is a general object of the present invention to provide methods and associated compositions for effectively modifying the immune system of a vertebrate to treat an immune disorder.

It is another object of the present invention to provide methods and compositions for the effective presentation of T cell receptor antagonists to modulate the cellular immune response in a subject in need thereof.

It is yet a further object of the present invention to provide methods and compositions for the treatment and amelioration of various immune disorders.

It is still another object of the present invention to provide for the relief of pathological symptoms associated with autoimmune disorders including multiple sclerosis.

SUMMARY OF THE INVENTION

These and other objectives are accomplished by the methods and associated compounds and compositions of the present invention which, in a broad aspect, provides for an Fc receptor mediated, endocytic delivery system. In selected embodiments the invention provides for the effective presentation of immunosuppressive factors which, in preferred embodiments may comprise T cell receptor antagonists. More particularly, the present invention provides methods, compounds and compositions to present immunosuppressive factors for the selective modification of an immune response in a vertebrate. In particularly preferred embodiments, the invention provides for Fc receptor mediated endocytic presentation of a selected T cell receptor antagonist to modulate an immune response mounted against a specific antigen. As will be appreciated by those skilled in the art, the disclosed methods and compositions may be used to treat any physiological disorder related to the immune response of a vertebrate. For example, this ability to suppress selected components of the immune system may allow, among other things, for the treatment of autoimmune diseases, facilitation of tissue or organ transplants and the mitigation of symptoms produced by allergens.

In preferred aspects of the invention, the endocytic presentation of the selected immunosuppressive factor is facilitated through the use of an immunomodulating agent that is able to bind to the Fc receptor (FcR) of antigen presenting cells. Typically, the immunomodulating agent will comprise at least one immunosuppressive factor associated with at least one ligand capable of binding to a Fc receptor. Upon binding to the antigen presenting cell (APC) the immunomodulating agent will be internalized and processed by the APC's natural endocytic pathway. Preferably, the internalized immunosuppressive factor, which can be a T cell receptor antagonist, will then be associated with the newly synthesized endogenous MHC class II structures and presented at the surface of the APC. Those skilled in the art will appreciate that the immunosuppressive factors, while complexing with T cell receptors when bound to MHC class II structures, will not promote activation of the T cell. It will further be appreciated that hundreds of TCR's on each T cell must be triggered in order to activate the cell. Accordingly, efficient presentation of the TCR antagonist can prevent a previously primed T cell (i.e. one sensitized to a particular antigen agonist) from activating and triggering an immune response despite competitive presentation of an antigen agonist.

In a broad sense, the immunomodulating agents of the present invention may comprise any ligand (FcR ligand) that is capable of binding to, and being internalized by, the Fc receptor of an antigen presenting cell. That is, the FcR ligand may be any protein, protein fragment, peptide or molecule that effectively binds to a Fc receptor on the surface of any antigen presenting cell. Preferably, the FcR ligand will comprise or mimic at least some portion of a constant region of an immunoglobulin molecule and will not provoke an antigenic response in the subject. In selected aspects of the invention, the FcR ligand will comprise part or all of a constant region from an IgG molecule. Particularly preferred embodiments will employ FcR ligands comprising the entire constant region of a selected immunoglobulin molecule from the species to be treated. Of course, it will also be appreciated that binding to the Fc receptor may also be effected by ligands that comprise small fragments of a single constant region domains or non amino acid based molecular entities. In any case, the FcR ligand may be derived using modern pharmaceutical techniques such as directed evolution, combinatorial chemistry or rational drug design.

As previously alluded to, the compounds of the present invention further comprise an immunosuppressive factor associated with the FcR ligand to provide an immunomodulating agent. For the purposes of the instant invention the immunosuppressive factor can be any molecular entity that is capable of being processed by an APC and presented in association with class II MHC molecules on the cell surface. In particularly preferred embodiments the immunosuppressive factor comprises all or part of a T cell antagonist. For the purposes of this disclosure the term "antagonist" shall, in accordance with its normal meaning, comprise any substance that interferes with the physiological action of another by combining with, and blocking, its receptor. More particularly, TCR antagonists are molecular entities that, in combination with class II MHC molecules, are capable of non-reactively associating with a T cell receptor and preventing that receptor from binding to its normal activating antigen ligand (i.e. an MHC-peptide agonist). Preferably, the TCR antagonist comprises a peptide or protein fragment that is an analog of the normal activating antigen agonist. In particularly preferred embodiments the TCR antagonist is an analog of a T cell epitope.

In the disclosed compounds and associated methods, the FcR ligand is associated with the immunosuppressive factor to form an immunomodulating agent so that both are internalized by the APC at substantially the same time. This association may be in the form of two or more molecules bound to each other as with an antibody-antigen complex or, in preferred embodiments, may comprise the formation of a single chimeric molecule incorporating both the immunosuppressive factor (i.e. a TCR antagonist) and FcR ligand. For example, a selected TCR antagonist could be chemically linked to an FcR ligand region produced by proteolytic techniques (i.e. an Fc fragment). Other embodiments may comprise a normal immunoglobulin comprising an FcR ligand sterically bound to an antagonistic peptide. Particularly preferred embodiments of the invention comprise chimeric immunoglobulins produced through genetic engineering techniques. In these compounds the FcR ligand (and usually the majority of the molecule) comprises one or more immunoglobulin constant regions while one or more of the variable regions is engineered to express a desired peptide TCR antagonist. Those skilled in the art will appreciate that any combination of the aforementioned immunomodulating agents may be associated to form compositions of the present invention as can similar immunomodulating agents comprising different immunosuppressive factors.

The disclosed compositions may be formulated using conventional pharmaceutical techniques and carriers and may be administered through the usual routes. However, the use of FcR mediated uptake of the immunomodulating agent avoids many of the problems associated with prior art compositions. More specifically, the methods of the present invention overcome many of the limitations associated with the administration of free peptide antagonists as disclosed in the prior art. Accordingly, efficient endocytic presentation of an immunosuppressive factor such as a TCR antagonist can generate significant levels of MHC-antagonist ligands to oppose abundant MHC-agonist complexes that are generated in spontaneous immune disorders involving the continuous presentation of antigen agonists. As such, the invention may be used to treat any immune disorder that responds to the presentation of immunosuppressive factors. This is particularly true of T cell mediated autoimmune disorders including, for example, multiple sclerosis, lupis, rheumatoid arthritis, scleroderma, insulin-dependent diabetes and ulcerative colitis. In a like manner, the present invention can be used to selectively downregulate the immune system with respect to continuously presented agonists such as allergens. Moreover, the compounds and associated compositions of the present invention may be used to selectively suppress various components of the immune system to reduce the likelihood of tissue or organ rejection following transplant.

Other objects, features and advantages of the present invention will be apparent to those skilled in the art from a consideration of the following detailed description of preferred exemplary embodiments thereof taken in conjunction with the figures which will first be described briefly.

BRIEF DESCRIPTION OF THE DRAWINGS

FIGS. 2A and 2B are graphical representations illustrating the capture of chimeric antibodies Ig-PLP1 and Ig-PLP-LR, which correspond to those shown in FIGS. 1A and 1B respectively, using antibodies directed to the corresponding free peptides wherein FIG. 2A shows capture levels by antibodies directed to PLP1 and FIG. 2B shows capture levels by antibodies directed to PLP-LR with Ig-W, a wild type antibody, acting as a negative control;

FIGS. 7A and 7B are graphs demonstrating the in vivo presentation of PLP1 following inoculation with Ig-PLP1 as measured by $^3$H-thymidine incorporation by cells from the lymph node (7A) or the spleen (7B) wherein the illustrated values represent the ability of cells harvested from individual mice to generate a T cell response as measured by $^3$H-thymidine incorporation when exposed to agonist PLP1 or the control peptide PLP2;

FIGS. 9A and 9B are graphs demonstrating that mice inoculated with a mixture of Ig-PLP-LR and Ig-PLP1 develop a more vigorous immune response to the peptide analog PLP-LR than peptide PLP1 as measured in cells from the lymph node (9A) or the spleen (9B) wherein the illustrated values represent the ability of cells harvested from individual subjects to generate a T cell response as reflected by $^3$H-thymidine incorporation when exposed to either PLP1 peptide or the peptide analog PLP-LR.

DETAILED DESCRIPTION OF THE PREFERRED EMBODIMENT

Figures 1A, 1B:
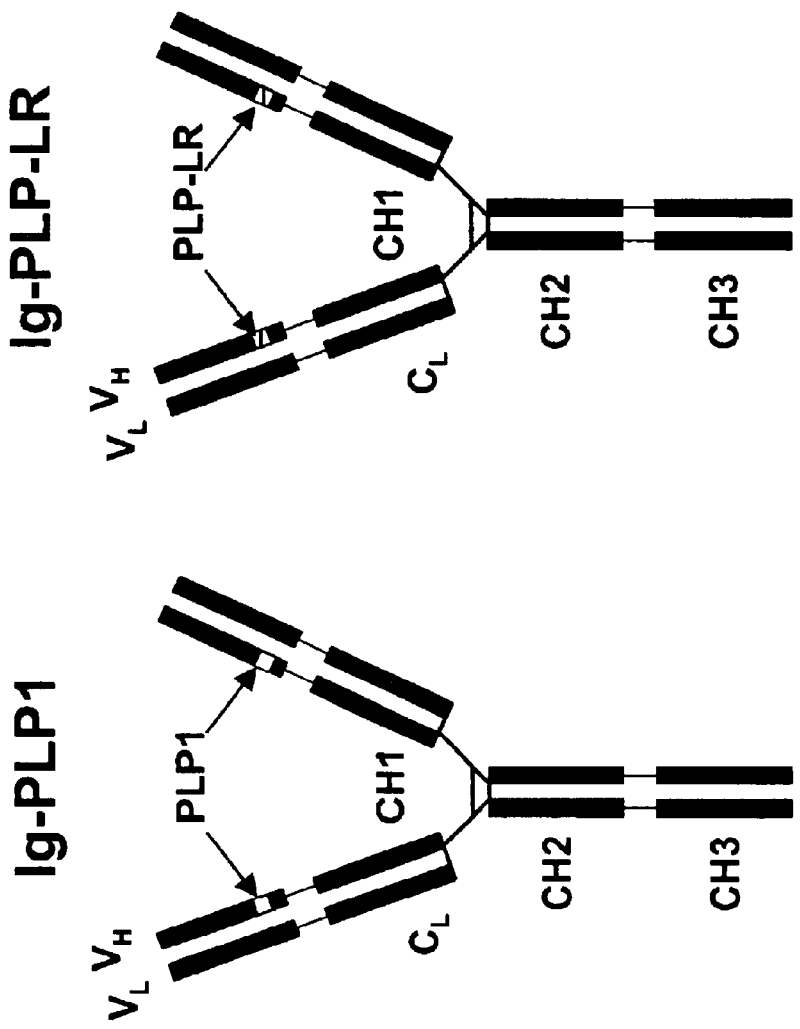
FIGS. 1A and 1B are schematic representations of chimeric immunoglobulin G (IgG) molecules illustrating the general features thereof and the inclusion of foreign peptides within the CDR 3 loop of the heavy chain variable region wherein FIG. 1A (Ig-PLP1) shows the insertion of a naturally occurring peptide (PLP1) derived from proteolipid protein while FIG. 1B (Ig-PLP-LR) illustrates an immunomodulating agent comprising the inclusion of a peptide analog (antagonist) to PLP1 termed PLP-LR.

While the present invention may be embodied in many different forms, disclosed herein are specific illustrative embodiments thereof that exemplify the principles of the invention. It should be emphasized that the present invention is not limited to the specific embodiments illustrated.

As previously alluded to, the present invention provides compounds, compositions and methods for selectively modifying the immune response of a vertebrate using an Fc receptor mediated endocytic delivery system. Essentially, any immunomodulating agent that can exploit this form of cellular uptake to downregulate the immune system is held to constitute part of the present invention. Among other forms, the immunomodulating agents of the invention may comprise single polypeptides, antigen-antibody complexes, chimeric antibodies or non-peptide based immunoactive compounds. In preferred embodiments the immunomodulating compounds disclosed herein will comprise at least one FcR ligand and at least one immunosuppressive factor that is capable of downregulating an immune response upon endocytic presentation. Particularly preferred embodiments of the invention comprise an immunomodulating agent wherein the immunosuppressive factor is a T cell receptor antagonist that is capable of binding with a receptor on the surface of a primed T cell but not capable of generating a response. In such embodiments, the presented TCR antagonist will effectively compete with selected naturally occurring TCR agonists preventing the activation of the corresponding primed T cells and reducing the response generated. This selective suppression of the immune system may, among other indications, be used to treat symptoms associated with immune disorders, including T cell mediated autoimmune disorders, allergies and tissue rejection in transplant operations.

Accordingly, in one embodiment the present invention comprises an immunomodulating agent for the endocytic presentation of an immunosuppressive factor on the surface of an antigen presenting cell of a vertebrate comprising at least one Fc receptor ligand and at least one immunosuppressive factor. Preferred embodiments comprise a Fc receptor ligand corresponding to at least a part of an immunoglobulin constant region domain while the immunosuppressive factor corresponds to at least one T cell receptor antagonist. In particularly preferred embodiments the immunomodulating agent comprises a recombinant polypeptide or a chimeric antibody.

By exploiting FcR mediated uptake of the selected immunomodulating agent the present invention very cleverly uses the body's own metabolic pathways to downregulate harmful immune responses. More specifically, the present invention uses the fact that T cells only recognize and respond to foreign antigens only when attached to the surface of other cells. Selection of the appropriate immunomodulating agent in accordance with the teachings herein provides for the efficient uptake of the administered compound. Following FcR mediated uptake, the natural endocytic pathway of antigen presenting cells provides for the effective presentation of the selected downregulating agent complexed with the MHC class II molecules.

As described above, the two requisite properties that allow a cell to function as an antigen presenting cell for class II MHC-restricted helper T cell lymphocytes are the ability to process endocytosed antigens and the expression of class II MHC gene products. Most cells appear to be able to endocytose and process protein antigens. Accordingly, the determining factor appears to be the expression of class II MHC molecules. In this respect, the best defined antigen presenting cells for helper T lymphocytes comprise mononuclear phagocytes, B lymphocytes, dendritic cells, Langerhans cells of the skin and, in some mammals, endothelial cells. Of course it will be appreciated that different cells may be concentrated in different areas and may be involved in different stages of the T cell mediated immune response. In any case, the term "antigen presenting cell" or "APC" as used herein shall be held to mean any cell capable of inducing a T cell mediated immune response through the processing and surface presentation of an MHC class II-antigen complex. As such, the selected FcR ligand may interact with any of a number of different Fc receptors found on a variety of cell types to promote endocytosis of the immunomodulating agent. By way of example only, selected human Fc receptors that may be employed include the FcγRI, FcγRIIA, FcγRIIB, FcγRIIIA or FcγRIIIB subfamilies.

More generally, in accordance with the present invention those skilled in the art will appreciate that any ligand capable of binding to an FcR complex and initiating endocytosis is compatible with the present invention and may be incorporated in the disclosed immunomodulating agents. Accordingly, FcR ligands may comprise, but are not limited to, peptides, proteins, protein derivatives or small molecular entities that may or may not incorporate amino acids. For example, small molecules derived using modern biochemical techniques such as combinatorial chemistry or rational drug design may be employed as long as they provide for the requisite APC uptake.

While it must be emphasized that any type of compatible molecule may be used, the FcR ligands of the present invention will preferably comprise one or more peptides. More preferably, the FcR ligand will comprise at least a part of a domain of a constant region of an immunoglobulin. In particularly preferred embodiments the FcR ligand will comprise one or more domains derived from a constant region of an immunoglobulin molecule. Those skilled in the art will appreciate that various immunoglobulin isotypes and allotypes may be employed as desired. For example, compatible FcR ligands may be selected from amino acid sequences corresponding to those found in the constant regions of IgG, IgE, IgA or IgM. Among other factors, selection of a particular isotype for use as a FcR ligand may be predicated on biochemical properties such as binding coefficients or low immunoreactivity in the species to be treated. Similarly, the selection of a single domain, fragment thereof or multiple domains may be determined based on biochemical factors or, ultimately, presentation efficiency.

Yet, efficient presentation via the endocytic pathway is typically not enough to selectively downregulate the immune response with regard to a particular antigen. Accordingly, immunomodulating agents of the present invention further comprise an immunosuppressive factor. In accordance with the scope of the present invention the immunosuppressive factor may be any compound that, when endocytically processed and presented on the surface of an APC in conjunction with a MHC class II complex, will downregulate the immune system. As such, immunosuppressive factors may comprise small molecules, peptides, protein fragments, or protein derivatives. In preferred embodiments the immunosuppressive factor acts as an antagonist when presented on the surface of the APC in that it interferes with the binding of a similarly presented agonist to a selected receptor. In particularly preferred embodiments the immunosuppressive factor comprises a T cell receptor antagonist that will associate with a T cell receptor without activating an immune response.

While any functionally compatible molecule may be used as an immunosuppressive factor in accordance with the present invention, those skilled in the art will appreciate that protein fragments or peptides are particularly suitable for use in the disclosed compounds and methods. Such molecules are readily processed by the normal endocytic pathways and are easily presented in concert with the MHC class II molecules on the surface of the antigen presenting cell. Moreover, as the majority of agonist compounds evoking an unwanted immune response are typically protein fragments, T cell receptors are usually most responsive to similar fragments. That is, as the T cell receptor must bind to the MHC class II-antagonist structure, the antagonist and agonist are preferably similar molecules. In particularly preferred embodiments, the immunosuppressive factor will be an analog of a selected peptide or protein fragment that is immunoreactive with a chosen T cell receptor.

"Peptide analogs" or "analogs," as used herein, contain at least one different amino acid in the respective corresponding sequences between the analog and the native protein fragment or peptide. Unless otherwise indicated a named amino acid refers to the L-form. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as B-alanine and homoserine. Also included with the scope of the present invention are amino acids which have been altered by chemical means such as methylation (e.g., a-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine).

Methods for selecting efficient peptide antagonists for treating multiple sclerosis (MS) are provided in PCT Publication No.: WO 96/16086 which has previously been incorporated into the instant application by reference. The disclosed methods may be used in concert with the present invention to provide effective immunosuppressive factors for incorporation in the disclosed immunomodulating agents. For example, using assays detailed below candidate peptide analogs may be screened for their ability to treat MS by an assay measuring competitive binding to MHC, T cell proliferation assays or an assay assessing induction of experimental encephalomyelitis (EAE). Those analogs that inhibit binding of the native peptides, do not stimulate proliferation of native peptide reactive cell lines and inhibit the development of EAE (an experimental model for MS) by native peptide are useful for therapeutics. Those skilled in the art will appreciate that similar types of assays may be used to screen immunosuppressive factors for other native peptides (i.e. continuously presented autoantigens) and other immune disorders. In particularly preferred embodiments T cell receptor antagonists comprise analogs of T cell epitopes.

More generally, immunosuppressive factors may be derived for a number of diseases having a variety of immunoreactive agents without undue experimentation. For example, peptide analog antagonists may be generated for T cell epitopes on both proteolipid protein or myelin basic protein to treat multiple sclerosis. Similarly, T cell receptor antagonists may be derived from T cell epitopes of the pyruvate dehydrogenase complex to treat primary biliary cirrhosis. In both cases the derived immunosuppressive factors will be incorporated in a immunomodulating agent as described herein and administered to a patient in need thereof. Effective presentation of the T cell receptor antagonist will selectively reduce stimulation of the autoreactive T cells by native peptide thereby relieving the symptoms of the subject immune disorder.

The selected immunosuppressive factor and FcR ligand, together comprising an immunomodulating agent, may be effectively administered in any one of a number of forms. More particularly, as described above, the immunomodulating agents of the present invention may combine any form of the respective elements that are functionally effective in selectively suppressing the immune response. For example, the immunomodulating agent may comprise a recombinant polypeptide or protein produced using modern molecular biology techniques. In such cases the FcR ligand may comprise a fragment of a single immunoglobulin region constant domain or, preferably, the entire constant region. In other embodiments the immunomodulating agent may comprise a sterically bound antibody-antigen complex wherein the antigen comprises a T cell receptor antagonist. Other preferred embodiments feature an immunomodulating agent comprising a chimeric antibody wherein an immunosuppressive factor is expressed on the Fab fragment. In still other embodiments the immunomodulating agent may comprise two covalently linked molecules which comprise a effective FcR ligand and immunosuppressive factor respectively.

Particularly preferred embodiments of the instant invention will employ recombinant nucleotide constructs to code for immunomodulating agents comprising a single fusion polypeptide. Those skilled in the art will appreciate that standard genetic engineering technology can provide fusion proteins or chimeras that will comprise at least one FcR ligand and at least one immunosuppressive factor. As used herein the terms "chimera" or "chimeric" will be used in their broadest sense to encompass any polynucleotide or polypeptide comprising sequence fragments from more than one source. For example, a genetically engineered polypeptide incorporating a peptide TCR antagonist and a single Fc domain from an IgG molecule could properly be termed a chimeric or fusion protein. Similarly, a chimeric antibody may comprise a recombinant heavy chains engineered to incorporate a heterologous peptide immunosuppressive factor and a wild type light chains. For the purposes of the present invention, it is not necessary that the disparate regions be derived from different species. That is, a chimeric antibody may comprise human light and heavy chains and an engineered human TCR antagonist expressed in a CDR. Conversely, chimeric immunomodulating agents may comprise FcR ligands and immunosuppressive factors derived from different species such a human and mouse.

As such, one aspect of the present invention comprises recombinant polynucleotide molecule encoding a polypeptide wherein said polynucleotide molecule comprises at least one nucleotide sequence corresponding to a Fc receptor ligand and at least one nucleotide sequence corresponding to an immunosuppressive factor. Preferably the immunosuppressive factor will correspond to a T cell receptor antagonist and the Fc receptor ligand corresponds to at least one constant region domain of an immunoglobulin. In a particularly preferred embodiment the polynucleotide molecule encodes a nucleotide sequence corresponding to an immunoglobulin heavy chain wherein a complementarity determining region has been at least partially deleted and replaced with a nucleotide sequence corresponding to T cell receptor antagonist.

In any case, DNA constructs comprising the desired immunomodulating agents may be expressed in either prokaryotic or eukaryotic cells using techniques well known in the art. See, for example, Maniatis, et al., *Molecular Cloning: A Laboratory Manual,* Cold Spring Harbor Laboratory, New York, 1982 which is incorporated herein by reference. In preferred embodiments the engineered plasmid will be transfected into immortal cell lines which secrete the desired product. As known in the art, such engineered organisms can be modified to produce relatively high levels of the selected immunomodulating agent. Alternatively, the engineered molecules may be expressed in prokaryotic cells such as *E. coli*. Whatever production source is employed, products may be separated and subsequently formulated into deliverable compositions using common biochemical procedures such as fractionation, chromatography or other purification methodology and conventional formulation techniques.

Accordingly, another aspect of the invention comprises a method for producing an immunomodulating agent for the endocytic presentation of an immunosuppressive factor on the surface of an antigen presenting cell of a vertebrate comprising the steps of:

a. transforming or transfecting suitable host cells with a recombinant polynucleotide molecule comprising a nucleotide sequence which encodes a polypeptide comprising at least one Fc receptor ligand and at least one immunosuppressive factor;

b. culturing the transformed or transfected host cells under conditions in which said cells express the recombinant polynucleotide molecule to produce said polypeptide wherein the polypeptide comprises at least a part of an immunomodulating agent; and c. recovering said immunomodulating agent.

Similarly, another aspect of the invention comprises transfected or transformed cells comprising a recombinant polynucleotide molecule encoding a polypeptide wherein the polypeptide comprises at least one Fc receptor ligand and at least one immunosuppressive factor.

In both of the preceding aspects, the immunosuppressive factor is preferably a T cell receptor antagonist and the Fc receptor ligand preferably comprises at least part of an immunoglobulin constant region domain. More preferably, the immunomodulating agent comprises a poly peptide or chimeric antibody wherein at least one complementarity determining region (CDR) has been replaced with a T cell receptor antagonist.

It will further be appreciated that the chimeric antibodies, polypeptides and other constructs of the present invention may be administered either alone, or as pharmaceutical composition. Briefly, pharmaceutical compositions of the present invention may comprise one or more of the immunomodulating agents described herein, in combination with one or more pharmaceutically of physiologically acceptable carriers, diluents or excipients. Such composition may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g. aluminum hydroxide) and preservatives. In addition, pharmaceutical compositions of the present invention may also contain one or more additional active ingredients, such as, for example, cytokines like B-interferon.

In this respect a further aspect of the present invention comprise pharmaceutical compositions for the endocytic presentation of an immunosuppressive factor on the surface of an antigen presenting cell of a vertebrate comprising at least one immunomodulating agent and a pharmaceutically acceptable carrier, said at least one immunomodulating agent comprising at least one Fc receptor ligand and at least one immunosuppressive factor. Similarly, the invention comprises methods for the preparation of a pharmaceutical composition to treat an immune disorder comprising combining at least one immunomodulating agent with a physiologically acceptable carrier or diluent wherein said immunomodulating agent comprises at least one Fc receptor ligand and at least one immunosuppressive factor. In both of these aspects the immunosuppressive factor may comprise a T cell receptor antagonist and the Fc receptor ligand may comprise at least part of a immunoglobulin constant region domain. Preferably, the immunomodulating agent will be in the form of a recombinant polypeptide or a chimeric antibody.

As indicated above, immunomodulating agents comprising chimeric antibodies are a particularly preferred aspect of the invention. Such antibodies may be formed by substituting a immunosuppressive factor, typically a peptide TCR antagonist, for at least part of one or more of the complementarity determining regions (CDR). As will be described more fully in the Examples below, the nucleotide sequence coding for the heavy chain may be engineered to replace all or part of at least one CDR with a peptide analog of a TCR agonist. Upon expression by the proper cell line, the recombinant heavy chains can complex with wild type light chains to form an immunoreactive tetramer displaying two peptide antagonists. Those skilled in the art will appreciate that the immunoglobulin molecules may be selected from the species to be treated so as to minimize the generation of a harmful immune response (i.e. a human anti-mouse response). As the constant region of the selected immunoglobulin is essentially unmodified, this form of immunomodulating agent is readily endocytosed allowing for effective presentation of the immunosuppressive factor.

In other forms, the immunomodulating agents of the present invention may comprise an antigen-antibody complex wherein the antigen is an immunosuppressive factor. It will be appreciated that modern immunological techniques may be used to generate and purify the desired antibodies which are preferably monoclonal. By way of example only, a selected peptide antagonist (i.e. an analog of a peptide antigen) may be injected into a mouse to provide immunoreactive cells which may then be harvested and immortalized using standard methods. If desired, the murine monoclonal may be "humanized" using conventional recombinant procedures leaving a small murine variable region expressed on an otherwise human immunoglobulin that will not provoke a harmful immune response in a patient. In any case, the monoclonal antibody is complexed with the immunosuppressive factor to form the desired immunomodulating agent which may then be formulated and administered as described above. With the intact constant region forming the FcR ligand, phagocytation should be relatively rapid and presentation of the attached immunosuppressive factor efficient.

Although embodiments may comprise the Fc receptor ligands corresponding to the entire constant region, it must be emphasized that the present invention does not require that the administered immunomodulating agent comprise an intact immunoglobulin constant region. Rather, any FcR ligand that can bind to the FcR and undergo endocytosis may be used in conjunction with the selected immunosuppressive factor. Specifically, single domains of constant regions or fragments thereof may be combined with peptide antagonists to form monomeric polypeptides (having a single amino acid chain) that can suppress the immune system in accordance with the teachings herein. Such fusion proteins may be constructed which, having the minimum effective FcR ligand and/or immunosuppressive factor, may be much more stable thereby facilitating delivery and possibly increasing bioavailability. Moreover, these engineered proteins may be able to be administered over a period of time without provoking an immune response as is seen when administering whole antibodies of heterologous species. As such, relatively small chimeric polypeptides may prove to be effective immunomodulating agents.

Similarly, non-peptide based molecular entities may prove to be efficient FcR ligands, immunosuppressive factors or, in combination, immunomodulating agents. Those skilled in the art will appreciate that molecular entities (peptide based or non-peptide based) that function effectively in a selected role (i.e. FcR ligand) may be provided using modern procedures such as combinatorial chemistry, directed evolution or rational drug design. For example, it may be possible to use rational drug design to fashion a small non-peptide molecular entity that effectively binds to a previously elucidated Fc receptor. The derived FcR ligand may then be covalently linked (or otherwise reversibly associated) with an immunosuppressive factor such as a peptide antagonist to provide an immunomodulating agent that exhibits particular stability or other desirable traits.

Whatever form of immunomodulating agent selected the compositions of the present invention may be formulated to provide desired stability and facilitate the selected form of administration. For example, the compositions may be administered using all the conventional routes including, but not limited to, oral, vaginal, aural, nasal, pulmonary, intravenous, intracranial, intraperitoneal, subcutaneous, or intramuscular administration. Within other embodiments of the invention, the compositions described herein may be administered as part of a sustained release implant. Within yet other embodiments, compositions of the present invention may be formulated as a lyophilizate or spray dried formulation, utilizing appropriate excipients which provide stability as a lyophilizate, and subsequent to rehydration.

The present invention is useful for the treatment of any vertebrate comprising an immune system subject to down regulation. The invention is particularly useful in those vertebrates such as mammals that possess cellular immune responses.

In this respect, a further aspect of the invention comprises a method for treating an immune disorder comprising administering to a patient a therapeutically effective amount of a pharmaceutical composition comprising an immunomodulating agent in combination with a physiologically acceptable carrier or diluent wherein said immunomodulating agent comprises at least one Fc receptor ligand and at least one immunosuppressive factor. For this aspect, the immunosuppressive factor may comprise a T cell receptor antagonist and the Fc receptor ligand may comprise at least part of a immunoglobulin constant region domain. As previously alluded to, the immunomodulating agent will preferably be in the form of a recombinant polypeptide or a chimeric antibody. The methods may be used treat immune disorders comprising autoimmune disorders, allergic responses and transplant rejection and are particularly useful in treating autoimmune disorders selected from the group consisting of multiple sclerosis, lupus, rheumatoid arthritis, scleroderma, insulin-dependent diabetes and ulcerative colitis.

Pharmaceutical compositions of the present invention may be administered in a manner appropriate to the disease to be treated (or prevented). The quantity and frequency of administration will be determined by such factors as the condition of the patient, and the type and severity of the patients disease. Within particularly preferred embodiments of the invention, the pharmaceutical compositions described herein may be administered at a dosage ranging from 1 μg to 50 mg/kg, although appropriate dosages may be determined by clinical trials. Those skilled in the art will appreciate that patients may be monitored for therapeutic effectiveness by MRI or signs of clinical exacerbation.

Following administration, the immunomodulating agent binds to one or more Fc receptors present on the surface of at least one type of antigen presenting cell. Those skilled in the art will appreciate that selection of the FcR ligand will, at least to some extent, determine which class of Fc receptor is used to internalize the immunomodulating agent. That is, a FcR ligand corresponding to an IgG constant region will be bound by a different class of Fc receptor than a FcR ligand corresponding to an IgE constant region. Moreover, as different classes of Fc receptors are expressed on different types of antigen presenting cells it is possible to present the immunosuppressive factor on selected APCs. For example, an FcR ligand corresponding to an IgG constant region is likely to be endocytosed by a macrophage or neutrophil and presented accordingly. This is of interest in that certain APCs are more efficient at presenting various types of antigens which, in turn, may influence which T cells are activated.

In any case, the entire immunomodulating agent is subjected to receptor mediated endocytosis by the APC and usually becomes localized in elathrin-coated vesicles. After internalization, the immunomodulating agent is processed for eventual presentation at the surface of the APC. Processing generally entails vesicle transport of the immunomodulating agent to the lyosome, an organelle comprising an acidic pH and selected enzymes including proteases. Here the immunomodulating agent is digested to provide a free immunosuppressive factor which, for the purposes of the instant invention, may be in the form of a peptide. In such cases average peptide lengths are on the order of 10 to 30 amino acids. Following digestion, at least some of the immunomodulating agent fragments, including the immunosuppressive factor fragment, are associated with MHC class II molecules in exocytic vesicles. The MHC class II-immunosuppressive factor complex is then transported to the surface of the APC and presented to helper T cells.

As pointed out above, preferred embodiments of the invention use a TCR antagonist as the immunosuppressive factor presented in concert with the class II MHC molecules. Accordingly, such antagonists (which may be peptide analogs) will be used for the purposes of the following discussion. However, it must be emphasized that the present invention may be used for the receptor mediated endocytic presentation of any immunosuppressive factor that downregulates an immune response.

Accordingly, by way of example only a T cell may have previously been sensitized to an autologous peptide agonist corresponding to a fragment of myelin basic protein. In multiple sclerosis this autoagonist is continuously presented thereby activating an immune response directed to constituents of the myelin sheath. More particularly, the sensitized individual T cells express thousands of receptors which selectively bind to the presented autoagonist and signal the cell. When enough of the receptors are bound, the sensitized T cell acts to mount a response i.e. secrete interleukin. In the cases where a TCR antagonist is presented in concert with MHC class II molecules the T cell will recognize the presented complex but will not be activated.

Thus, in accordance with the present invention efficient endocytic presentation of an antagonist inhibits agonist-TCR binding through competition for the receptors. That is, the present TCR antagonist binds effectively to the TCR of a sensitized T cell thereby precluding binding of a presented agonist. Yet, unlike an agonist-TCR complex, an antagonist-TCR complex does not signal the T cell to mount a response.

Thus, the competitive binding of the antagonist can prevent a T cell from binding enough agonist to reach the threshold activation level that induces the cell to act. Hence, a harmful immune response to the continuously presented autoantigen comprising the agonist is averted.

Presentation of the following non-limiting Examples will serve to further illustrate the principles of the present invention. In this regard, a list of abbreviations and corresponding definition used throughout the following discussion and the Examples is provided:

MBP: myelin basic protein, has been implicated in the etiology of multiple sclerosis;

PLP: proteolipid protein, has been implicated in the etiology of multiple sclerosis;

PLP1: a peptide fragment of PLP comprising aa residues 139–151;

PLP-LR: a peptide analog of PLP1, does not activate PLP1 pulsed cells;

PLP2: a peptide fragment of PLP comprising aa residues 178–191;

Ig-W: an Ig construct (used herein as a control) comprising the heavy chain variable region of the anti-arsonate antibody 91A3, linked to a Balb/cγ2b constant region, and the parental 91A3 kappa light chain;

Ig-PLP1: the same construct as Ig-W except that the heavy chain CDR3 was replaced with aa residues 139–151 of PLP;

Ig-PLP-LR: the same construct as Ig-W except that the heavy chain CDR3 was replaced with a peptide analog of aa residues 139–151 of PLP;

Ig-HA: (used as a control herein) the same construct as Ig-W except that the heavy chain CDR3 was replaced with aa residues 110–120 of influenza virus HA;

PPD: purified protein derivative, whole *Mycobacterium tubercuolosis* extract used as a control activator.

For obvious practical and moral reasons, initial work in humans to determine the efficacy of experimental compositions or methods with regard to many diseases is infeasible. Thus, during early development of any drug it is standard procedure to employ appropriate animal models for reasons of safety and expense. The success of implementing laboratory animal models is predicated on the understanding that immunodominant epitopes are frequently active in different host species. Thus, an immunogenic determinant in one species, for example a rodent or pig, will generally be immunoreactive in a different species such as in humans. Only after the appropriate animal models are sufficiently developed will clinical trials in humans be carried out to further demonstrate the safety and efficacy of a vaccine in man. Accordingly, for purposes of explanation only and not for purposes of limitation, the present invention will be primarily demonstrated in the exemplary context of mice as the mammalian host. Those skilled in the art will appreciate that the present invention may be practiced with other mammalian hosts including humans and domesticated animals.

In this respect, experimental encephalomyelitis (EAE), which is used as an animal model for MS, can be induced in susceptible strains of mice with myelin autoantigens such as PLP and myelin basic protein (MBP). The encephalitogenic activity of these proteins correlates with the presence of peptides which induce in vivo class II restricted encephalitogenic T cells and consequently EAE. The peptide corresponding to aa residues 139–151 of PLP (PLP1) is encephalitogenic in H-2s SJL mice, and T cell lines specific for PLP1 transfer EAE into naive animals. Although the target antigen(s) in human MS is still debatable, the frequency of T cells specific for myelin proteins are higher in MS patients than in normal subjects. Silencing those myelin-reactive T cells may be a logical approach to reverse MS. As such, this model will be used to demonstrate the advantages of the present invention.

EXAMPLE I

Preparation of Peptides

For the purposes of this application the amino acids are referred to by their standard three-letter or one-letter code. Unless otherwise specified, the L-form of the amino acid is intended. When the 1-letter code is used, a capital letter denotes the L-form and a small letter denotes the D-form. The one letter code is as follows: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; and Y, tyrosine.

All peptides used in the following examples were produced by Research Genetic, Inc. (Huntsville, Ala.) using solid state methodology and purified on HPLC columns to >90% purity using conventional methods. PLP1 peptide (HSLGKWLGHPNKF: SEQ. ID No. 1) encompasses an encephalitogenic sequence corresponding to aa residues 139–151 of naturally occurring proteolipid protein. PLP-LR (HSLGKLLGRPNKF: SEQ. ID No. 2) is an analog of PLP1 in which Trp144 and His147 were replaced with Leu and Arg (underlined), respectively. PLP1 and PLP-LR bind well to I-A$^S$ class II molecules (i.e. an MHC class II structure produced by a specific strain of mice). PLP2 peptide (NTWTTCQSIAFPSK: SEQ. ID No. 3) encompasses an encephalitogenic sequence corresponding to aa residues 178–191 of PLP. This peptide also binds to I-A$^S$ class II molecules and induces EAE in SJL mice. HA peptide (sequence not shown) corresponds to aa residues 110–120 of the hemagglutinin of the Influenza virus. HA binds to I-E$^D$ class II molecules and is used here as control peptide.

EXAMPLE II

Production of Murine Chimeric Immunoglobulins Comprising Exogenous Peptides

Two immunoglobulin-peptide chimeras, designated Ig-PLP1 and Ig-PLP-LR and shown schematically in FIG. 1, were constructed to express peptides PLP1 and PLP-LR as described in Example 1. In both cases, the heavy chain CDR 3 loop was deleted and replaced with nucleotide sequences coding for the selected peptide. Conventional DNA sequencing analysis indicated insertion of peptide nucleotide sequences in the correct reading frame.

The genes used to construct these chimeras include the gene coding for the BALBK IgG$_2$b constant region as described by Gillian et al., *Cell*, 33:717,1983, the gene coding for the 91A3 heavy chain variable region as described by Ruthban et al., *J. Mol. Bio.*, 202:383–398, 1988, and the gene coding for the entire 91A3 kappa light chain as described by Gary et al., *Proc. Natl. Acad. Sci.*, 84:1085–1089, 1987, all of which are incorporated herein by reference. The procedures for deletion of the heavy chain CDR3 region and replacement with nucleotide sequences coding for PLP1 and PLP-LR are similar to those described by Zaghouani et al. *J. Immunol.* 148: 3604–3609, 1992 and incorporated herein by reference, for the generation of Ig-NP a chimera carrying a CTL epitope corresponding to aa residues 147–161 of the nucleoprotein of PR8 influenza A virus. The same reference reports that the CDR3 of the 91A3 IgG is compatible for peptide expression, and that both class I and class II-restricted epitopes have been efficiently processed and presented to T cells when grafted in place of the naturally occurring segment.

Briefly, The 91A3$V_H$ gene was subcloned into the EcoRI site of pUC19 plasmid and used as template DNA in PCR mutagenesis reactions to generate 91A3$V_H$ fragments carrying PLP1 (91A3$V_H$-PLP1) and PLP-LR (91A3$V_H$-PLP-LR) sequences in place of CDR3. Nucleotide sequencing analysis indicated that full PLP1 and PLP-LR sequences were inserted in the correct reading frame (not shown). The 91A3$V_H$-PLP1 and 91A3$V_H$-PLP-LR fragments were then subcloned into the EcoRI site of pSV2-gpt-Cγ2b in front of the exons coding for the constant region of a Balb/cγ2b which generated pSV2-gpt-91A3$V_H$-PLP1-Cγ2b and pSV2-gpt-91A3$V_H$-PLP1-LR-Cγ2b plasmids, respectively. These plasmids were then separately cotransfected into the non-Ig producing SP2/0 B myeloma cells with an expression vector carrying the parental 91A3 light chain, pSV2-neo-91A3L. Transfectants producing Ig chimeras were selected in the presence of geneticin and mycophenolic acid. Transfectants were cloned by limiting dilution and final clones secreted 1 to 4 μg/mL of Ig-PLP1 or Ig-PLP-LR (collectively, the Ig-PLP chimeras). The selected cell lines, designated Ig-PLP1-9B11 and Ig-PLP-LR-21A10, are maintained in permanent storage in the inventor's laboratory.

Chimeric and wild-type antibodies were also used as controls. For example Ig-Ha, and IgG molecule carrying in place of the D segment the HA110-120 T helper epitope from the HA of influenza virus that differs from Ig-PLP1 and Ig-PLP-LR only by the peptide inserted within CDR3. Ig-W is the product of unmodified (wild-type) 91A3$V_H$ gene, Balb/cγ2b constant region and 91A3 kappa light chain. Therefore it differs from Ig-PLP1 and Ig-PLP-LR in the CDR3 region which comprises the parental D segment. Finally, Ig-PLP2, is a chimeric antibody that carries within the heavy chain CDR3 loop aa residues 178–191 of PLP. Conventional cloning, sequencing, and purification procedures were used to generate the appropriate cell lines and are similar to those described by Zaghouani et al. (previously cited) and those previously used to generate Ig-HA, Zaghouani et al., *Science*, 259:224–227, 1993 also incorporated herein by reference.

Large scale cultures of transfectants were carried out in DMEM media containing 10% iron enriched calf serum (Intergen, New York). Ig-PLP chimeras were purified from culture supernatant on columns made of rat-anti-mouse kappa chain mAb and coupled to CNBr activated Sepharose 4B (Pharmacia). Rat-anti-mouse kappa chain mAb (RAM 187.1 or ATCC denotation, HB-58) and mouse anti-rat kappa light chain mAb (MAR 18.5 or ATCC denotation, TIB 216) were obtained from the ATCC. These hybridomas were grown to large scale and purified from culture supernatant on each other. The rat anti-mouse kappa mAb was used to prepare the columns on which the Ig-PLP chimeras were purified from culture supernatant. To avoid cross contamination separate columns were used to purify the individual chimeras.

EXAMPLE III

Purification of Proteolipid Protein

Native proteolipid protein or PLP was purified from rat brain according to the previously described procedure of Lees et al., in *Preparation of Proteolipids, Research Methods in Neurochemistry*, N. Marks and R. Rodnight, editors, Plunemum Press, New York, 1978 which is incorporated herein by reference.

Briefly, brain tissue was homogenized in 2/1 v/v chloroform/methanol, and the soluble crude lipid extract was separated by filtration through a scintered glass funnel. PLP was then precipitated with acetone and the pellet was redissolved in a mixture of chloroform/methanol/acetic acid and passed through an LH-20-100 sephadex column (Sigma) to remove residual lipids. Removal of chloroform from the elutes and conversion of PLP into its apoprotein form were carried out simultaneously through gradual addition of water under a gentle stream of nitrogen. Subsequently, extensive dialysis against water was performed to remove residual acetic acid and methanol.

EXAMPLE IV

Production of Rabbit Anti-peptide Antibodies

PLP1 and PLP-LR peptides prepared in Example I were coupled to KLH and BSA as described in Zaghouani et al., *Proc. Natl. Acad. Sci USA*. 88:5645–5649, 1991 and incorporated herein by reference. New Zealand white rabbits were purchased from Myrtle's Rabbitry (Thompson Station, Tenn.). The rabbits were immunized with 1 mg peptide-KLH conjugates in complete Freund's adjuvant (CFA) and challenged monthly with 1 mg conjugate in incomplete Fruend's adjuvant (IFA) until a high antibody titer was reached. The peptide-BSA conjugates were coupled to sepharose and used to purify anti-peptide antibodies from the rabbit anti-serum.

EXAMPLE V

Characterization of Rabbit Anti-peptide Antibodies

Capture radioimmunoassays (RIA) were used to assess expression of PLP1 and PLP-LR peptides on an IgG molecule using Ig-PLP1 and Ig-PLP-LR made as described in Example II.

Microtiter 96-well plates were coated with the rabbit anti-peptide antibodies made in Example IV (5 μg/mL) overnight at 4° C. and blocked with 2% BSA in PBS for 1 hour at room temperature. The plates were then washed 3 times with PBS, and graded amounts of Ig-PLP1 and Ig-PLP-LR were added and incubated for 2 hours at room temperature. After 3 washes with PBS, the captured Ig-PLP1 and Ig-PLP-LR were detected by incubating the plates with 100×10$^3$ cpm $^{125}$I-labeled rat anti-mouse kappa mAb for 2 hours at 37° C. The plates were then washed 5 times with PBS and counted using an LKB gamma counter. Shown are the mean±SD of triplicates obtained with 27 μg/mL of chimeras.

Figures 2A, 2B:
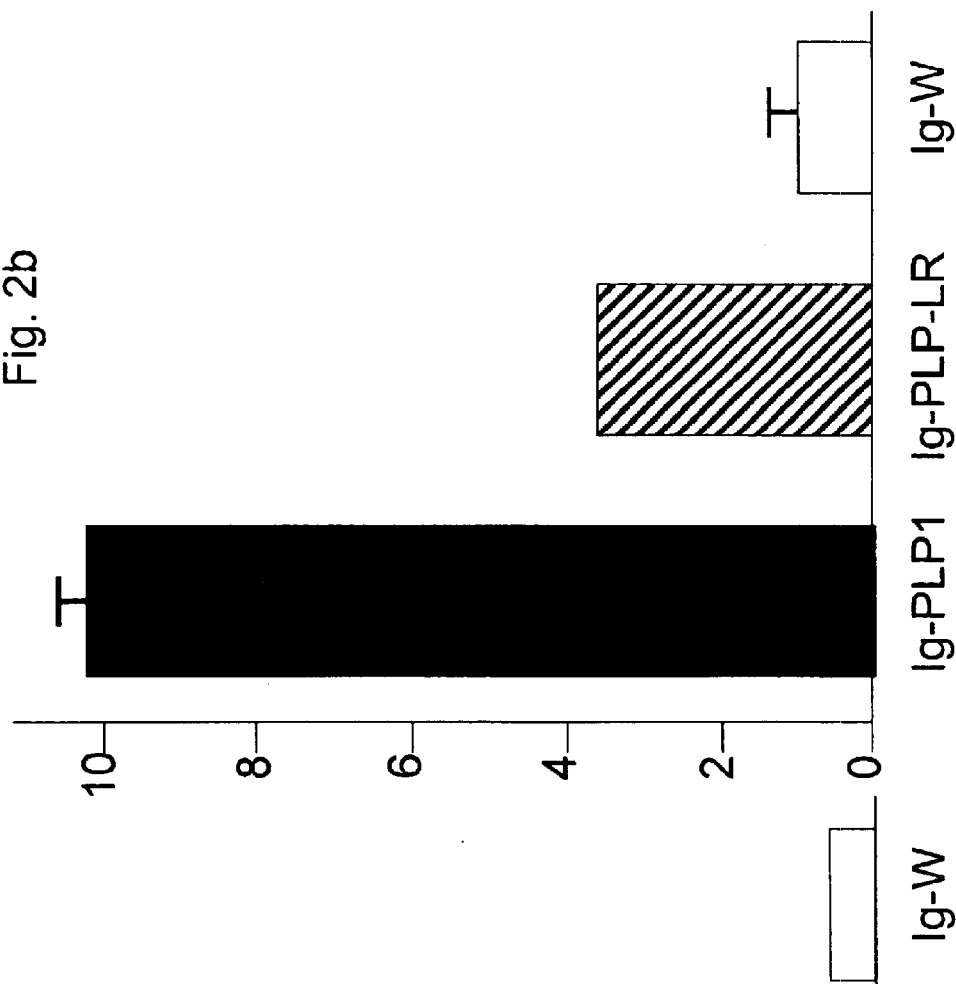

As shown in FIG. 2, the rabbit antibodies directed to synthetic PLP1 and PLP-LR peptides recognized the chimeric antibodies Ig-PLP1 and Ig-PLP-LR produced in Example II. More specifically, when Ig-PLP1 and Ig-PLP-LR were incubated on plates coated with rabbit anti-PLP1 they were captured in significant quantity and bound labeled rat anti-mouse kappa chain mAb (FIG. 2A). Similarly, both Ig-PLP1 and Ig-PLP-LR were captured by rabbit anti-PLP-LR (FIG. 2B). Conversely, Ig-W, the wild type 91A3 murine antibody without an exogenous peptide and an IgM control antibodies (not shown), did not show significant binding to the rabbit antibodies. Ig-PLP1 bound to both anti-PLP1 and anti-PLP-LR better than did Ig-PLP-LR, indicating that structural differences affected accessibility of the peptides to the rabbit antibodies. Further, the results shown in FIG. 2 indicate that peptide expression on the chimeras did not alter heavy and light chain pairing because the rabbit antibodies bind to the PLP peptide on the heavy chain and the labeled rat anti-mouse kappa binds on the light chain.

EXAMPLE VI

Antigen Specific T Cell Line Proliferation Assays

PLP1-specific T cell hybridomas 5B6 and 4E3 and the IL-2 dependent HT-2 T helper cells were obtained from The Eunice Kennedy Shriver Center, Waltham, Mass. The 5B6 and 4E3 T cells recognize the peptide PLP1 in association with 1-$A^S$ class II MHC and produces IL-2 when incubated with it as reported by Kuchroo et al., *J. Immunol.* 153:3326–3336, 1994 which is incorporated herein by reference. Conversely, Kuchroo et al. report that when stimulated with PLP1 and then with PLP-LR both 5B6 and 4E3 cells no longer produce IL-2. Similarly, stimulation of T cell hybridomas with PLP1 in the presence of PLP-LR apparently inhibits IL-2 production.

Using substantially the same technique as Kuchroo et al., activation of the T cell hybridomas for various agonists was performed as follows. Irradiated (3,000 rads) splenocytes from SJL mice were used as antigen presenting cells (APCs) for this Example. The irradiated splenocytes were incubated in 96-well round bottom plates ($5 \times 10^5$ cells/well/50 $\mu$l) with graded concentrations of antigens (100 $\mu$l/well). After one hour, T cell hybridomas, i.e. 5B6 of 4E3 ($5 \times 10^4$ cells/well/50 $\mu$l) were added and the culture was continued overnight. Activation (or proliferation) of the T cells was assessed by measuring production of IL-2 in the culture supernatant. This was done by $^3$H-thymidine incorporation using the IL-2 dependent HT-2 cells. That is, when IL-2 is present (i.e. secreted by activated T cells) the HT-2 cells proliferate, incorporating labeled thymidine from the surrounding media.

The culture media used to carry out these assays was DMEM supplemented with 10% FBS, 0.05 mM 2-mercaptoethenol, 2 mM glutamine, 1 mM sodium puryvate and 50 $\mu$g/mL gentamycin sulfate. Briefly, culture supernatants (100 $\mu$l/well) were incubated with HT-2 cells ($1 \times 10^4$ cells/well/100 $\mu$l) in 96-well flat bottom plates for 24 hours. Subsequently 1 $\mu$Ci $^3$H-thymidine was added per well and the culture was continued for an additional 12–14 hours. The cells were then harvested on glass fiber filters and the non incorporated $^3$H-thymidine was washed away. Incorporated thymidine was then counted using the trace 96 program and an Inotech β counter. It will be appreciated that those wells containing higher levels of IL-2 (secreted by the activated T cell hybridoma lines) will induce higher levels of HT-2 cell proliferation and register increased levels of $^3$H-thymidine incorporation.

Figures 3A, 3B:
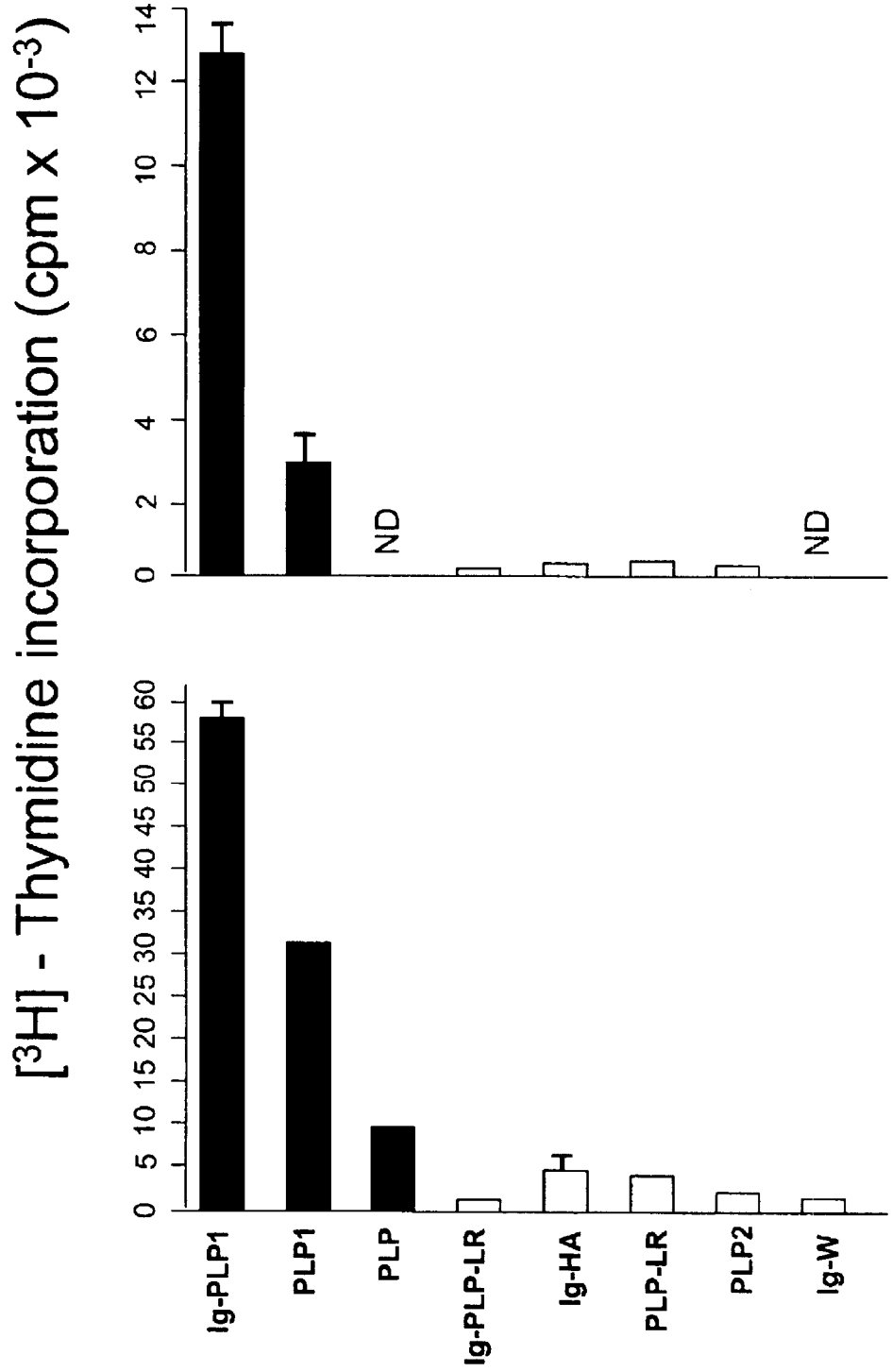
FIGS. 3A and 3B are graphs illustrating the presentation of Ig-PLP1 and Ig-PLP-LR (as well as positive and negative controls) to PLP1-specific T cell hybridomas 4E3 (FIG. 3A) and 5B6 (FIG. 3B) to determine the relative T cell activation potentials of the chimeric immunoglobulins as measured by IL-2 production.

The results of the aforementioned assay using two different T cell lines are shown in FIG. 3. Specifically, T cell hybridomas 4E3 (FIG. 3A) and 5B6 (FIG. 3B) produced substantial levels of IL-2 following stimulation by APCs previously incubated with Ig-PLP1, PLP1 and native PLP. The negative controls Ig-W, Ig-HA, and PLP2 peptide did not induce the production of IL-2 by the T cells. Similarly, both Ig-PLP-LR and PLP-LR peptide did not stimulate 5B6 and 4E3 to produce significant levels of IL-2. These last results are not unexpected because the PLP-LR peptide is known to negate rather than stimulate IL-2 production. The concentration of antigen was 0.1 $\mu$M for Ig-PLP1, Ig-PLP-LR, Ig-HA, and Ig-W; 1 $\mu$M for PLP1, and PLP2 peptides; and 1.7 $\mu$M for PLP. Each value represents the mean±SD of triplicate wells.

These results indicate that Ig-PLP1 was presented to the T cell hybridomas in a manner conducive to activation. Steric hindrance appears to preclude the simultaneous direct binding of the whole antibody to the MHC structure and TCR. As T cells will not react to soluble proteins, it appears that the PLP1 peptide was released from the Ig by endocytic processing and bound MHC class II I-$A^S$ molecules. Accordingly, the regions flanking the PLP1 peptide do not appear to interfere with the endocytic processing of Ig-PLP1 or the binding of the PLP1 peptide to the MHC class II structure.

EXAMPLE VII

Presentation of PLP1 Peptide to T Cells Via Ig-PLP1

In spontaneous immune disorders, exposure and continuous endocytic presentation of an autoantigen may generate significant levels of MHC-agonist complexes. Currently many immune diseases lack an effective in vitro model for replicating this continuous presentation affording a serious impediment to the development of effective treatments. Due to relatively inefficient internalization mechanisms or the previously discussed limitations relating to free peptides, relatively high levels of natural antigens are required to provide the desired stimulation. Accordingly, one aspect of the present invention is to provide an in vitro model for the continuous endocytic presentation of agonist ligands.

More particularly, the present invention provides methods for the effective in vitro endocytic presentation of a T cell antagonist comprising the steps of:
 a. providing a medium comprising a plurality of antigen presenting cells expressing Fc receptors; and
 b. combining said medium with a immunomodulating agent containing composition wherein the composition comprises an immunomodulating agent having at least one Fc receptor ligand and at least one immunosuppressive factor and a compatible carrier.

Preferably the immunosuppressive factor will be at least one T cell receptor antagonist and the Fc receptor ligand will be at least part of a immunoglobulin constant region domain. Further, in preferred aspects of the invention the immunomodulating agent will comprise a recombinant polypeptide or a chimeric antibody.

In this respect, Ig-PLP1 (or any immunoglobulin associated agonist) may be used for the purpose of establishing a peptide delivery system that could efficiently operate through the endocytic pathway and generate high levels of agonist ligands such that it provides an in vitro system to investigate the immune system. In particular, the disclosed may be used to investigate antagonism in a situation similar to the in vivo presentation of autoantigens.

To demonstrate that immunoglobulin associated agonists may be used to mimic continuous endocytic presentation of antigens, T cell activation assays were performed with free PLP1 peptide, native PLP, and Ig-PLP1. The results of the assays are shown in FIG. 4.

Specifically, different concentrations of the three antigens (i.e. agonists) were incubated with irradiated SJL/J splenocytes which were subsequently associated with 4E3 T cell hybridomas. IL-2 production was measured by $^3$H-thymidine incorporation using the IL-2 dependent HT-2 cells as described in Example VI. Each point represents the mean of triplicates. The standard deviation did not exceed 10% of the mean value.

Figure 4:
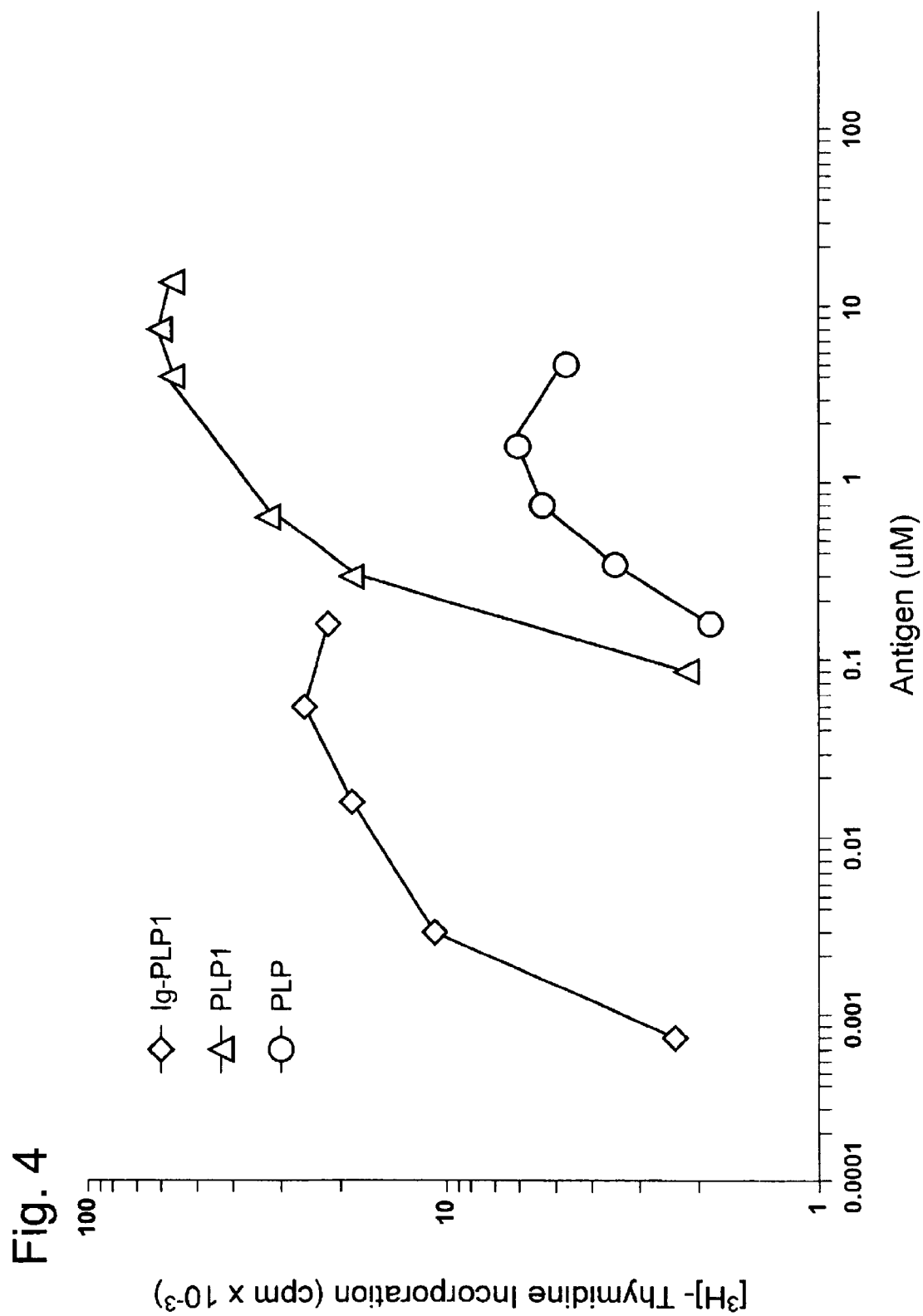
FIG. 4 is a graphical representation illustrating the relative effectiveness of presenting PLP1 using the chimeric antibodies of the present invention (Ig-PLP1) versus the free peptide PLP1 or the native proteolipid protein (PLP) as measured by levels of IL-2 production following incubation with splenic SJL antigen presenting cells and PLP1 specific 4E3 T cell hybridoma.

FIG. 4 shows that, although the maximum activation levels varied among the three different agonists, the levels required to stimulate the T cells were much lower for Ig-PLP1 than for either free PLP1 or native PLP. That is, it took substantially less Ig-PLP1 to stimulate the cell line than either the native PLP or the free peptide (on the order of 1/100). Specifically, stimulation to half the maximum level required less Ig-PLP1 (0.005 $\mu$M) than PLP (0.5 $\mu$M) or PLP1 peptide (0.6 $\mu$M). These results indicate that the PLP1 T cell epitope is better presented by Ig-PLP1 than by native PLP or by synthetic PLP1 peptide. Although the plateau of IL-2 production was higher when the T cell activator is free PLP1 synthetic peptide it requires substantially higher agonist levels that may be difficult to obtain in vivo over an extended period.

While not limiting the present invention in any way, it appears that the efficacy of Ig-PLP1 in peptide delivery is related to FcR mediated internalization and access to newly synthesized MHC molecules. More particularly, native PLP appears to internalize rather ineffectively by simple fluid phase pinocytosis while free PLP1 peptide appears to simply bind to empty MHC class II molecules at the cell surface. The ineffectual presentation of these forms of the autoantigen is clearly illustrated by FIG. 4 which unambiguously shows that Ig-PLP1 is more efficient in presenting PLP1 peptide in combination with MHC class II molecules than either the free peptide or the native protein.

EXAMPLE VIII

Inhibition of T Cell Activation In vitro

Antagonism of PLP1, PLP, and Ig-PLP1 T cell activation by Ig-PLP-LR was detected using a prepulsed proliferation assay.

Irradiated (3,000 rads) SJL splenocytes (used as APCs) were incubated in 96-well round bottom plates (5×10$^5$ cells/well/50 $\mu$l) with the selected agonist (1 $\mu$M PLP1 peptide, 0.05 $\mu$M Ig-PLP1 or 7 $\mu$M PLP) and various concentrations of antagonist (100 $\mu$l/well) for 1 hour. Subsequently, 4E3 T cell hybridomas (5×10$^4$ cells/well/50 $\mu$l) were added and the culture was continued overnight. IL-2 production in the supernatant, determined as in Example VI using HT-2 cells, was used as measure of T cell activation. The results of this assay are shown in FIG. 5.

Figures 5A, 5B, 5C:
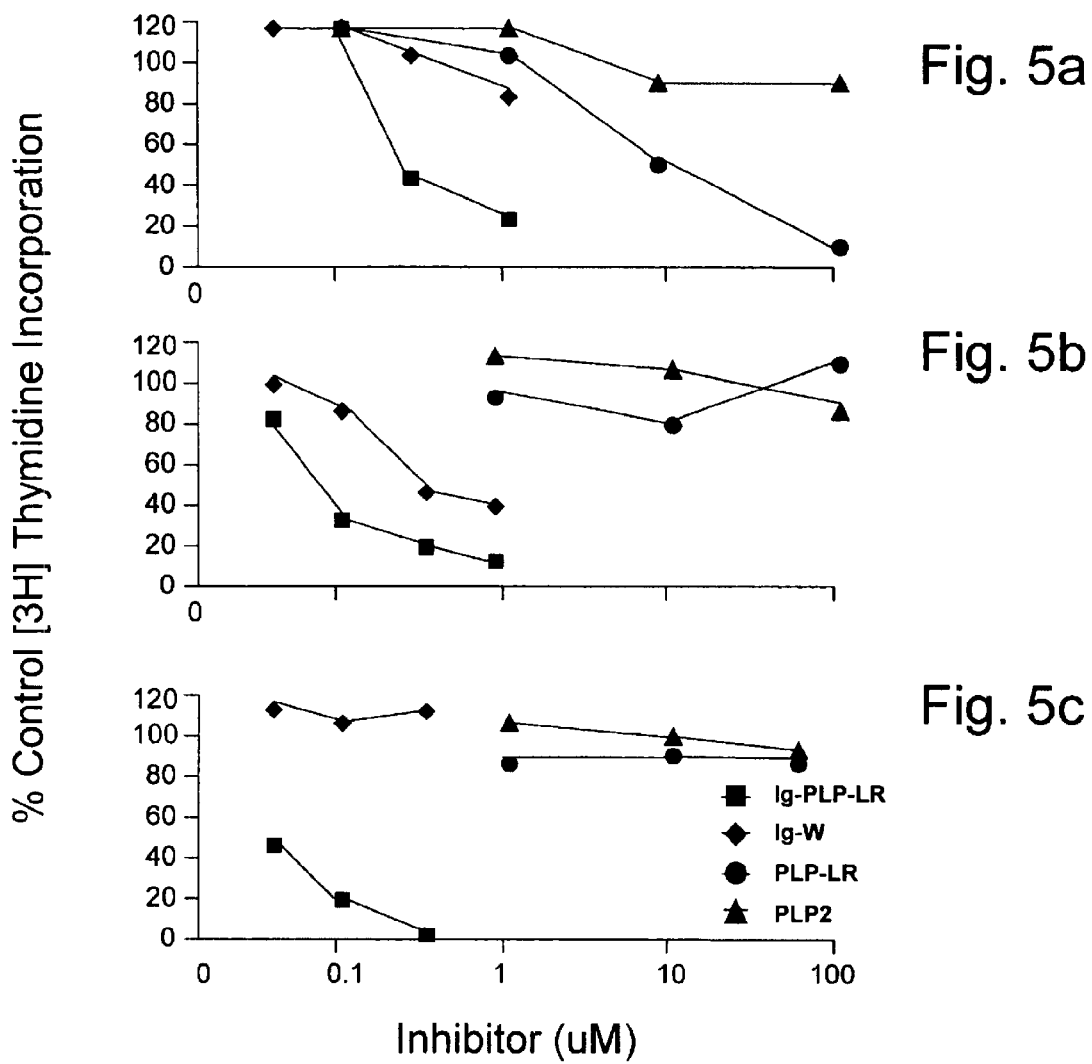
FIGS. 5A, 5B and 5C are graphical comparisons showing Ig-PLP-LR antagonism of PLP1 (5A), Ig-PLP1 (5B) and PLP (5C) mediated T cell activation as measured by IL-2 production by T cell hybridoma 4E3 in the presence of SJL splenic APCs that were previously incubated with the respective agonist and various levels of Ig-PLP-LR or controls.

More particularly, FIGS. 5A, 5B and 5C show antagonism of free PLP1 peptide (5A), Ig-PLP1 chimeric immunoglobulin (5B) and native PLP (5C) respectively. The antagonists were Ig-PLP-LR (squares) and PLP-LR (circles) with controls of Ig-W (diamonds) and PLP2 (triangles).

Cpm values obtained when the APCs were incubated with the agonist but no antagonist was used as control thymidine incorporation. This value was 7,503±1,302 for Ig-PLP1; 31,089±3,860 for PLP1 peptide; and 8,268±915 for PLP. The cpm value obtained when the APCs were incubated with no agonist or antagonist was used as background (BG). This value was 1,560±323 for Ig-PLP1; 2,574±290 for PLP1 peptide; and 2,127±177 for PLP. The percent control thymidine incorporation was calculated as follows: [(cpm obtained in the presence of test antagonist)–(BG)]/[(cpm control thymidine incorporation value)–(BG)]. Each point represents the mean of triplicates.

As previously discussed, the potency of Ig-PLP1 chimeras in peptide loading onto MHC class II molecules may resemble in vivo autoimmune circumstances where a continuous supply of antigen often allows for abundant generation of self peptides which can trigger T cell aggressively.

FIG. 5A (PLP1 agonist) shows that when T cells were incubated with APCs in the presence of both PLP1 and Ig-PLP-LR, a substantial decrease in IL-2 production occurred as the concentration of Ig-PLP-LR increased. A similar decline in IL-2 production was evident when the synthetic PLP-LR peptide was used during T cell activation with PLP1 peptide. Conversely, antagonist effects were not observed with the control Ig-W immunoglobulin and the PLP2 peptide. Inhibition of IL-2 production to half the maximum level (60% control thymidine incorporation) required only 0.4 $\mu$m Ig-PLP-LR versus 9 $\mu$M PLP-LR peptide indicating a much more efficient presentation of, and T cell antagonism by, Ig-PLP-LR.

Further evidence that the chimeric immunoglobulin is more efficient than the free peptide in T cell antagonism is shown in FIGS. 5B and 5C. Specifically, FIG. 5B shows that Ig-PLP-LR inhibited T cell activation mediated by Ig-PLP1 while free PLP-LR, like the negative control PLP2 peptide, did not show any significant antagonism. Significantly, FIG. 5B also shows that Ig-W, the wild type 91A3 immunoglobulin without any exogenous peptide exhibits partial inhibitory activity in Ig-PLP1 mediated T cell activation. It is believed that this may be the result of competition for binding to the FcR on the APCs because both Ig-PLP1 and Ig-W share identical IgG2b constant regions. A maximum of 50% inhibition in IL-2 production was seen when the activation of T cells by Ig-PLP1 was carried out in the presence of Ig-W. Thus, Ig-W would compete with Ig-PLP1 for FcR binding and internalization thereby diminishing the activation of T cells. That is, as the concentration of Ig-W increases, less Ig-PLP1 will bind to FcR and be internalize by the APCs resulting in a diminished presentation and corresponding IL-2 production. It is important to note that this Ig-W mediated reduction in response is not the result of antagonistic effects but rather simply a result of competition for FcR binding. That is, the presented Ig-W epitopes are not TCR antagonists for PLP1 and do not interact with the PLP1 specific TCRs.

In contrast to FIG. 5B, FIG. 5C shows that Ig-PLP-LR, but not Ig-W, significantly reduces the activation of T cells by native PLP. As Ig-W is likely internalized in a different manner than native PLP, (Fc receptor versus simple fluid phase pinocytosis) there should not be any direct competition for uptake and processing and hence no inhibition.

For the sake of convenience the results shown in FIG. 5 are summarized in Table 1 immediately below. When APCs were incubated with PLP1 peptide in the presence of Ig-PLP-LR there was no activation of the PLP1-specific T cell hybridomas (FIG. 5a). Moreover, when the activation of T cells by native PLP and Ig-PLP1 was carried out in the presence of various concentrations of Ig-PLP-LR, IL-2 production (i.e. T-cell activation) declined as Ig-PLP-LR increased. However, free PLP-LR peptide failed to inhibit T cell activation mediated by native PLP or Ig-PLP1. These two lines of evidence indicate that the principal mechanism for Ig-PLP-LR mediated inactivation of T cells was likely to be endocytic presentation and TCR antagonism rather than direct blockage of MHC class II molecules on the cell surface.

In the table below a plus sign indicates inhibition of IL-2 production and therefore antagonism, while a minus sign indicates little or no inhibition of IL-2 production and therefore little or no antagonism.

TABLE 1

Ig-PLP-LR and PLP-LR Mediated T Cell Antagonism.

| Antagonist | Stimulator (Agonist) | | |
|---|---|---|---|
| | PLP1 | PLP | Ig-PLP1 |
| PLP-LR | + | − | − |
| Ig-PLP-LR | + | + | + |

The results of the foregoing example indicate that the FcR mediated uptake and subsequent processing of a peptide antagonist are compatible with efficient presentation by the antigen presenting cell. This is extremely unexpected in view of the prior art where the delivery of free peptide analogs was assumed to provide efficient antagonism through direct competition for MHC or TCR binding sites.

EXAMPLE IX

Characterization of Mechanism for Antagonism by Ig-PLP-LR

Using an assay similar to the one performed in Example VIII, it was demonstrated that competition for direct binding to the Fc receptor is not, in and of itself, a likely mechanism for Ig-PLP-LR mediated antagonism.

Figure 6:
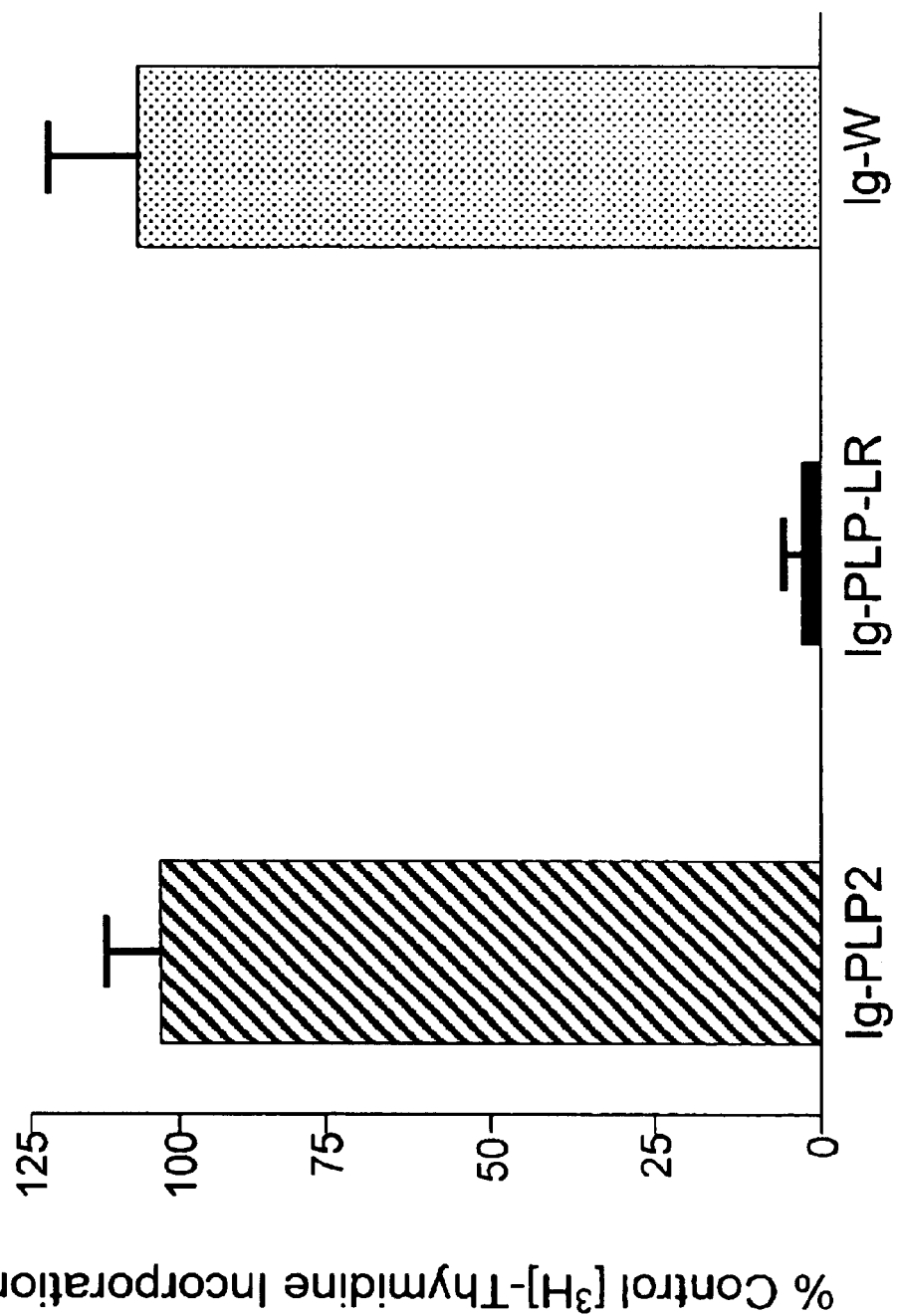
FIG. 6 is a graph showing the relative antagonism of Ig-PLP2, Ig-PLP-LR and Ig-W as measured by the production of IL-2 by T cell hybridoma HT-2 in the presence of SJL splenic APCs that were previously incubated with native proteolipid protein in combination one of the aforementioned immunoglobulins.

SJL splenic APCs were incubated with native PLP (6.8 $\mu$M) in the presence of 2 $\mu$M Ig-PLP2, Ig-PLP-LR, or Ig-W and assayed for IL-2 production by $^3$H-thymidine incorporation using HT-2 cells as described in the previous Examples. Ig-PLP2 was prepared as in Example II using the sequence detailed in Example I. The % control thymidine incorporation was calculated as in Example VIII. Results of the assay are shown in FIG. 6 wherein each column represents the mean±SD of triplicates.

As with the results shown in FIG. 5B, the present Example supports the position that both efficient presentation on the MHC class II structure and an effective peptide analog provide the mode significant results. That is, even though the Ig-PLP2 chimeric antibody is taken up and processed, efficient presentation of the PLP2 peptide by I-A$^s$ will not preclude activation of the T-cells as it is not an analog of the native PLP agonist. Accordingly, simple competition binding to MHC class II molecules on the antigen presenting cells is not likely to produce the desire antagonism.

EXAMPLE X

In vivo Induction of a T Cell Response to PLP1

By this Example it was demonstrated that, in addition to generating a T cell response in vitro (Example VII), the chimeric antibodies of the present invention could be used to generate a cellular response in vivo. Specifically, the following Example demonstrates the in vivo priming of PLP1 specific T cells by Ig-PLP1.

Six to eight week old SJL mice (II-2$^s$) were purchased from Harlan Sprague Dawley (Frederick, Md.) and maintained in an animal facility for the duration of experiments.

The mice were immunized subcutaneously in the foot pads and at the base of the limbs and tail with 50 $\mu$g of Ig-PLP1 emulsified in a 200 $\mu$l mixture of 1:1 v/v PBS/CFA. Ten days later the mice were sacrificed by cervical dislocation, the spleens and lymph nodes (axillary, inguinal, popliteal, and sacral) were removed, single cell suspension were prepared, and the T cell responses were analyzed. The results shown in FIG. 7 are those obtained with $4\times10^5$ lymph node cells/well (7A) and $10\times10^5$ spleen cells/well (7B). The activators PLP1 and PLP2 were used at 15 $\mu$g/mL and PPD was used at 5 $\mu$g/mL.

As with the previous Examples, T cell activation was monitored using a proliferation assay comprising $^3$H-thymidine incorporation. Here, lymph node and spleen cells were incubated for three days in 96-well round bottom plates, along with 100 $\mu$l of a single selected activator, at 4 and $10\times10^5$ cells/100 $\mu$l/well, respectively. Subsequently, 1 $\mu$Ci $^3$H-thymidine was added per well, and the culture was continued for an additional 12–14 hours. The cells were then harvested on glass fiber filters, and incorporated $^3$H-thymidine was counted using the trace 96 program and an Inotech $\beta$ counter. A control media with no stimulator was included for each mouse and used as background.

Each value shown in FIG. 7 was calculated as described in Example VIII and represents the mean±SD of triplicates after deduction of background cpms obtained with no activator in the media. Similar results were obtained when mice were immunized with 150 $\mu$g of Ig-PLP per mouse (not shown).

FIGS. 7A and 7B clearly show that, when Ig-PLP1 was injected subcutaneously in the foot pads and at the base of the limbs and tail, a strong specific T cell response to the PLP1 peptide was induced. While there was some variation as to the strength of the reaction among the individual mice, the lymph node and spleen cells of each produced a significant response upon challenge with the PLP1 peptide. Interestingly there is a significant PLP1 specific response detected in the spleen, an organ that mostly filters and responds to systemic antigens. One possibility that can be put forth to explain these results is that Ig-PLP1, because of it's long half life, was able to circulate and reach both the lymphatic and blood circulation and consequently be presented at both systemic and lymphatic sites. This is potentially very beneficial when implementing therapeutic regimens for autoimmune disorders. It was also interesting that some mice show proliferation when the cells are stimulated with PLP2 peptide in vitro. Possibly, the fact that this peptide is presented by I-A$^s$ like PLP1 allows low affinity cells to bind and generate a response. In any case the results are consistent with those provided by the earlier Examples where it was shown that Ig-PLP1 was efficient in presenting the peptide to T cells in vitro.

EXAMPLE XI

In vivo Inhibition of a T Cell Response to PLP1

As seen in the previous Example, Ig-PLP1 is capable of priming T cells in vivo and generates a potent immune response when exposed to the agonist PLP1 peptide. This Example demonstrates that the administration of a peptide antagonist in the form of a chimeric antibody immunomodulating agent can substantially reduce the immune response generated by the endocytic presentation of an agonist ligand. Specifically, this Example demonstrates that co-administration of Ig-PLP-LR with Ig-PLP1 significantly reduces the immune response to PLP1 peptide.

Mice were co-immunized with mixtures of either 50 $\mu$g Ig-PLP1 and 150 $\mu$g Ig-PLP-LR or 50 $\mu$g Ig-PLP1 combined with 150 $\mu$g Ig-W. In particular, individual mice from three groups (4 mice per group) were injected sc, as in Example X with a 200 μl mixture (PBS/CFA, 1:1 v/v) containing one of the following mixtures: 50 μg Ig-PLP1 and 150 μg Ig-PLP-LR; 50 μg Ig-PLP1 and 150 μg Ig-W; or Ig-PLP1 and 100 μg PLP-LR peptide. Splenic and lymph node T cell responses were analyzed at day 10 post immunization using the protocol set forth in Example X. The lymph node cells were assayed at $4 \times 10^5$ cells/well and the spleen cells at $10 \times 10^5$ cells/well. The agonist ligand was PLP1 at 15 μg/mL. Results for the lymph node and spleen cells, shown in FIGS. 8A and 8B respectively and summarized in Table 2 below, represent the mean±SD of triplicates after deduction of background cpm obtained with no agonist in the media.

Figure 8A:
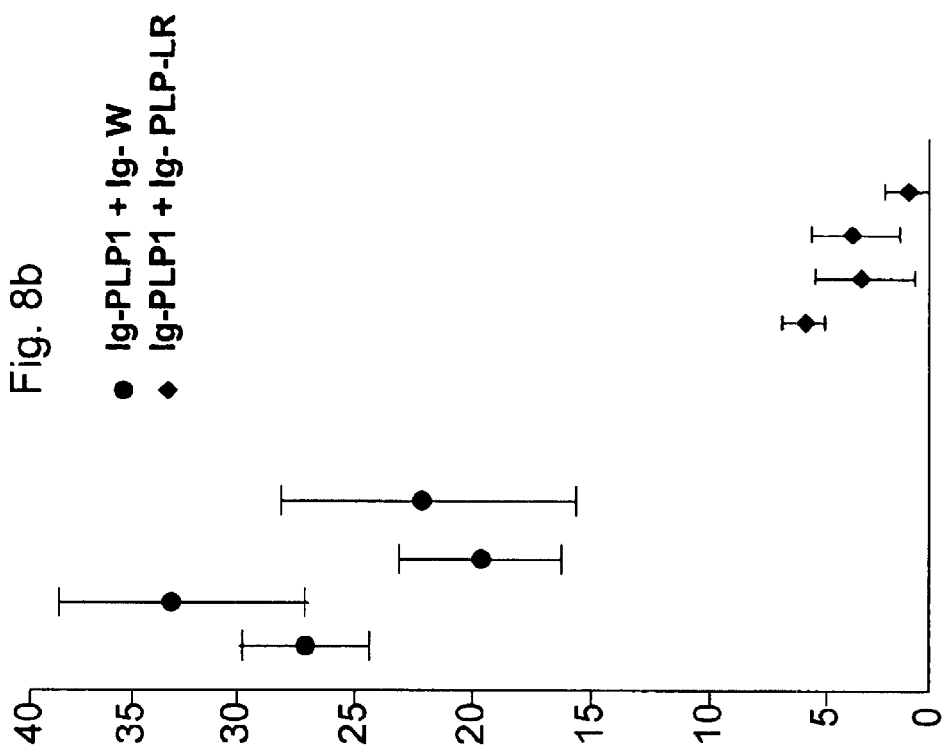
FIGS. 8A and 8B are graphical representations showing the ability of Ig-PLP-LR to reduce the immune response to PLP1 peptide when co-administered with Ig-PLP1 as measured in murine cells from the lymph node (8A) or the spleen (8B) wherein the illustrated values represent the ability of cells harvested from individual mice to generate a T cell response as measured by $^3$H-thymidine incorporation when exposed to PLP1.
Figure 8B:
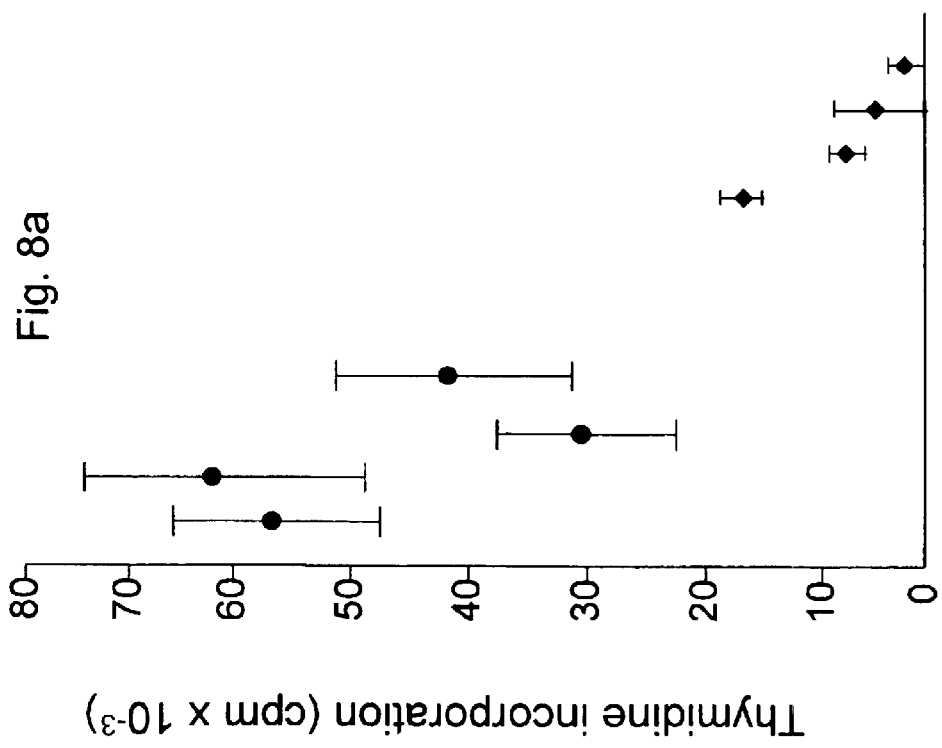

FIGS. 8A and 8B show that, although Ig-PLP1 was efficiently presented and induced a strong in vivo T cell response (Example X), it was possible to antagonize such a response by including Ig-PLP-LR in the mixture administered to mice. Indeed, when Ig-PLP1 was co-administered to mice with Ig-PLP-LR, the subsequent immune response to free PLP1 peptide was markedly reduced as shown on the right half of FIGS. 8A and 8B. It appears that the low PLP1 response for both the spleen and lymph node tissue was a result of PLP-LR antagonism, since the co-administration with Ig-PLP1 of the wild type antibody, Ig-W, did not significantly reduce the T cell response. These results strongly indicate that it is the efficient in vivo presentation of PLP-LR through the FcR binding and endocytic processing of Ig-PLP-LR that is responsible for the reduced cellular response.

Moreover, as seen in Table 2 immediately below, when free PLP-LR peptide was co-administered with Ig-PLP1 there was no indication that the PLP1 response was reduced. The numbers provided in the table represent the percentage values of PLP1 specific proliferation relative to PPD specific proliferation and were derived as follows:
(mean cpm of triplicates obtained with PLP1 stimulation−mean cpm triplicate BG)/(mean cpm of triplicates obtained with PPD−mean cpm triplicate BG)×100

TABLE 2

Ig-PLP-LR But Not Free PLP-LR Peptide Mediates T Cell Antagonism In Vitro

| | Ig-PLP1 co-administered with: | | |
|---|---|---|---|
| Mouse | Ig-W | Ig-PLP-LR | PLP-LR peptide |
| | | PLP1/PPD (%) | |
| 1 | 100 | 28 | 81 |
| 2 | 95 | 40 | 91 |
| 3 | 78 | 37 | 93 |
| 4 | 79 | 25 | 100 |

The results above clearly show that co-administration of the free antagonist peptide or the control Ig-W lacking an antagonist peptide have little effect on the generated immune response. The lack of antagonist effect by free PLP-LR peptide was not due to a net lower amount of injected peptide because the mice were given approximately 34 fold more PLP-LR in the free peptide form than in the Ig-PLPLR form (on the basis of a MW of 150,000 D, the 150 μg of Ig-PLP-LR given to the mice correspond to 1 nmole of Ig that contains 2 nmoles of PLP-LR peptide, while with a MW of 1,468 Daltons the 100 μg of free PLP-LR peptide corresponds to 68 nmoles of peptide). The failure of PLP-LR peptide to inhibit Ig-PLP1 mediated T cell activation coupled with the potency of Ig-PLP-LR in antagonizing Ig-PLP1 T cell stimulation supports the belief that Ig-PLP-LR mediated in vivo antagonism is likely related to efficient presentation.

EXAMPLE XII

Induction of a T Cell Response to an Endocytically Presented Antagonist

Previous Examples have shown that administration of chimeric antibodies comprising a agonist ligand can prime immune cells in vivo. It was also shown that administration of a chimeric antibody comprising an antagonist can reduce a subsequent response to challenge by an agonist ligand. This Example demonstrates that efficient presentation of an antagonist can prime immune cells in vivo and mount a strong response that could effect the reaction of the T cells to an agonist peptide. Specifically, mice co-injected with Ig-PLP1 and Ig-PLP-LR develop a relatively high proliferative response to PLP-LR and practically no response to PLP1 peptide.

Lymph node and spleen cells were obtained in the same manner as set forth in Example X following co-administration of Ig-PLP1 and Ig-PLP-LR. Proliferative responses in individual mice were also measured using the methods set out in the previous Example following in vitro stimulation with either free PLP1 peptide or PLP-LR peptide at 15 μg/mL. The results of the assays using lymph node and spleen cells are detailed in FIGS. 9A and 9B respectively.

As can be seen from FIG. 9, both spleen and lymph nodes developed responses to the antagonist PLP-LR but not to the PLP agonist PLP1. Knowing that Ig-PLP-LR induced PLP-LR specific T cells when it was co-administered with Ig-PLP1, it can be speculated that these PLP-LR-specific T cells downregulate PLP1 specific T cells. Conversely, although there was induction of PLP-LR-specific response when free PLP-LR peptide was administered with Ig-PLP1 (not shown), there was no evident reduction in the proliferative response to PLP1. Accordingly, the data set forth in the instant example demonstrates that the use of chimeric antibodies comprising an antagonist are much more effective for modulating the immune response to an antigen agonist than the free peptide antagonist.

More particularly, in view of the foregoing examples it appears that TCR engagement with PLP-LR-I-$A^S$ complexes (i.e. MHC-PLP-LR complexes) on the surface of APCs antagonizes T cells rather than stimulates them. Accordingly, antagonism by Ig-PLP-LR may occur because efficient presentation of Ig-PLP-LR in endocytic vacuoles ensures significant levels of PLP-LR-I-$A^S$ complexes (antagonist complexes) are generated. The amount of complexes on the cell surface is proportional to the amount of Ig-PLP-LR offered to the APCs. When PLP1 stimulation is carried out in the presence of Ig-PLP-LR, both PLP-LR-I-$A^S$ and PLP1-I-$A^S$ are present on the surface of a given APC where an increase in the concentration of Ig-PLP-LR leads to higher number of PLP-LR-I-$A^S$ complexes. It will be appreciated that approximately 3500 TCR have to be engaged in order for a T cell to be activated and that a given complex of MHC class II-peptide complex serially engages approximately 200 TCRs. As such, it appears that a T cell is antagonized when TCR engagement with PLP-LR-I-$A^S$ complexes override engagement with the agonist PLP1-I-$A^S$. Overall, because of efficient loading of PLP-LR by Ig-PLP-LR, T cell antagonism is achieved by a higher frequency of serial triggering of TCR by PLP-LR-I-$A^S$ complexes. That is, the efficient uptake and processing of Ig-PLP-LR simply means that too many of the surface MHC complexes present the PLP-LR antagonist to allow the remaining surface complexes presenting the PLP1 agonist ligand to engage the number of TCRs to activate the T cell.

Therefore, the T cells will not be activated as long as the antagonist is presented at a rate that ensures that activation concentration of MHC class II-agonist complexes is not reached on the APC.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the invention.

What is claimed is:

1. A composition comprising an immunoglobulin or a portion thereof linked to a protein fragment or peptide, wherein said immunoglobulin or portion thereof is capable of binding to an Fc receptor and said protein fragment or peptide comprises a T cell receptor antagonist, said composition having the property of being endocytosed by cells bearing said Fc receptor and processed by the cells to present said T cell receptor antagonist in association with endogenous MHC Class II molecules, thereby preventing activation of autoreactive T cells in vivo.

2. The composition of claim 1, further comprising a pharmaceutically acceptable carrier.

3. The composition of claim 1, wherein said protein fragment or peptide comprising a T cell receptor antagonist is covalently linked to said immunoglobulin or portion thereof.

4. The composition of claim 3, wherein said protein fragment or peptide comprising a T cell receptor antagonist comprises a peptide analog of proteolipid protein.

5. The composition of claim 3, wherein said immunoglobulin or portion thereof comprises at least part of a domain of a constant region of an immunoglobulin molecule.

6. The composition of claim 2, wherein the composition comprises a fusion protein in which said protein fragment or peptide comprising a T cell receptor antagonist is covalently joined to said immunoglobulin or portion thereof.

7. The composition of claim 6, wherein said protein fragments or peptide comprising a T cell receptor antagonist is positioned within at least one complementarity determining region to partially or fully replace said complementarity determining region.

8. The composition of claim 1, wherein said T cell receptor antagonist is derived from proteolipid protein.

9. The composition of claim 1 wherein said T cell receptor antagonist derived from proteolipid protein is a peptide analog of proteolipid protein.

10. The composition of claim 1 wherein said immunoglobulin or portion thereof comprises at least part of a domain of a constant region of an immunoglobulin molecule.

11. The composition of claim 1 wherein the composition comprises a fusion protein in which said protein fragment or peptide comprising a T cell receptor antagonist is covalently joined to said immunoglobulin or portion thereof.

12. The composition of claim 11 wherein the protein fragment or peptide comprising said T cell receptor antagonist is positioned within at least one complementarity determining region to partially or fully replace said complementarity determining region.

13. The composition of claim 1 wherein said protein fragment or peptide comprising a T cell receptor antagonist comprises a peptide analog of a peptide which induces a T cell response.

14. The composition of claim 2 wherein said immunoglobulin or portion thereof comprises at least part of one domain of a constant region of an immunoglobulin molecule.

15. The composition of claim 14 wherein the immunoglobulin or portion thereof is a human IgG molecule or portion thereof.

16. The composition of claim 15 wherein said composition comprises a fusion protein in which said protein fragment or peptide comprising a T cell receptor antagonist is covalently joined to said immunoglobulin or portion thereof.

* * * * *